United States Patent
Kuhn

(10) Patent No.: US 8,489,164 B2
(45) Date of Patent: Jul. 16, 2013

(54) MONITORING OF TISSUE HEMOGLOBIN CONCENTRATION

(75) Inventor: Jonathan L. Kuhn, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 468 days.

(21) Appl. No.: 12/913,096

(22) Filed: Oct. 27, 2010

(65) Prior Publication Data
US 2012/0108925 A1 May 3, 2012

(51) Int. Cl.
*A61B 5/1455* (2006.01)

(52) U.S. Cl.
USPC .......................................... 600/310; 600/476

(58) Field of Classification Search
USPC .................. 600/310, 322, 323, 328, 473, 476
See application file for complete search history.

(56) References Cited

U.S. PATENT DOCUMENTS

| | | | |
|---|---|---|---|
| 5,830,133 A | 11/1998 | Osten | |
| 5,879,294 A | 3/1999 | Anderson | |
| 5,931,779 A * | 8/1999 | Arakaki et al. | 600/310 |
| 6,192,261 B1 | 2/2001 | Gratton et al. | |
| 6,473,632 B1 | 10/2002 | Myers | |
| 6,599,250 B2 | 7/2003 | Webb | |
| 7,120,478 B2 | 10/2006 | Cho | |
| 7,536,214 B2 | 5/2009 | Myers | |
| 7,613,489 B2 | 11/2009 | Myers | |
| 2005/0002031 A1 | 1/2005 | Kraemer et al. | |
| 2007/0093701 A1 | 4/2007 | Myers | |

FOREIGN PATENT DOCUMENTS

| | | |
|---|---|---|
| WO | 00/30530 | 6/2000 |
| WO | 00/77495 | 12/2000 |

OTHER PUBLICATIONS

Rajaram, N., "Lookup table-based inverse model for determining optical properties in turbid media", Journal of Biomedical Optics; Sep. 22, 2008; pp. 1-3; vol. 13(5), USA.
Myers, D. "Tissue Hemoglobin Index (THI): A noninvasive optical measure of total tissue hemoglobin." Critical Care; 2009;13(Suppl 5): S2, USA.
Myers, et al., "Noninvasive Method for Measuring Local Hemoglobin Oxygen Saturation in Tissue Using Wide Gap Second Derivative Near-Infrared Spectroscopy" Journal of Biomedical Optics, Spie—International Society for Optical Engineering, vol. 10, No. 3, May 2005, 18 pages.
(PCT/US2011/057424) PCT Notification of transmittal of the International Search Report and the Written Opinion of the International Searching Authority, Mailed Apr. 17, 2012, 13 pages.

* cited by examiner

*Primary Examiner* — Eric Winakur
(74) *Attorney, Agent, or Firm* — Evans M. Mburu; Stephen W. Bauer; Michael C. Soldner

(57) ABSTRACT

A medical device system and associated method monitor tissue hemoglobin concentration. Light attenuation is measured in a volume of tissue in a patient. A value of a tissue scattering coefficient corresponding to the tissue volume in the patient is established in response to the attenuation measurement. A second derivative of the light attenuation measurement is determined. An artifact correction term is computed in response to the established tissue scattering coefficient, and a tissue hemoglobin concentration is computed using the artifact correction term and the second derivative.

21 Claims, 14 Drawing Sheets

US 8,489,164 B2

MONITORING OF TISSUE HEMOGLOBIN CONCENTRATION

TECHNICAL FIELD

This disclosure relates generally to medical devices and, in particular, to a medical device system and associated method for monitoring tissue hemoglobin concentration (THC) in patients.

BACKGROUND

Implantable medical devices (IMDs) are available for monitoring and treating patients for a variety of conditions. Such devices often include physiological sensors for sensing signals correlated to physiological events or conditions. The detection or monitoring of physiological events or conditions is used for diagnosing a patient condition, determining a need for therapy or medical intervention, and sometimes for controlling a therapy delivered automatically by the implantable device.

Tissue oxygen saturation ($O_2$Sat) is one variable that can be monitored to assess a patient condition. Optical sensors are available or have been proposed for monitoring $O_2$Sat (sometimes referred to as $StO_2$) or an index of $O_2$Sat. A number of factors can influence $O_2$Sat measured at a body tissue site. Lung function, cardiac function, consumption of oxygen at the tissue site, and other factors can influence $O_2$Sat measurements. As such, other monitored physiological signals may be needed in conjunction tissue $O_2$Sat, along with clinical patient examination, in order to infer a patient condition.

DETAILED DESCRIPTION

Figure 1:
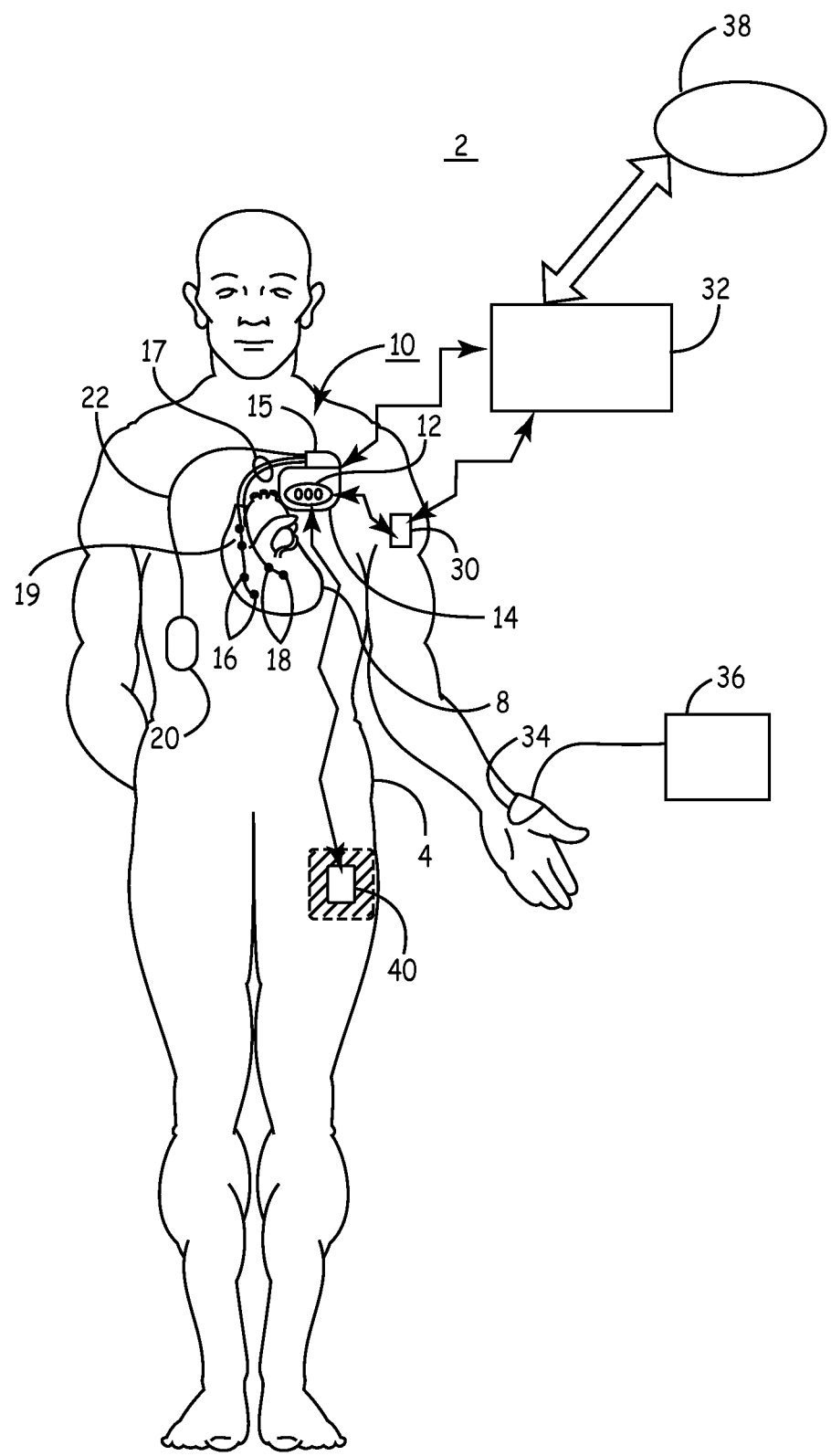
FIG. 1 is a schematic view of a medical device system for monitoring a patient.

In the following description, references are made to illustrative embodiments. It is understood that other embodiments may be utilized without departing from the scope of the disclosed method and apparatus. In some instances, for purposes of clarity, the same reference numbers may be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

The availability of oxygen at a tissue site will depend in part on tissue hemoglobin concentration (THC). THC at a tissue site may vary with blood hematocrit level, cardiac function (e.g. cardiac output) and local vascular tension among other factors. As such, monitoring THC can be useful in monitoring the status of local tissue as well as interpreting the meaning of other physiological data, such as $O_2$Sat, in terms of a local condition at the tissue site or a systemic patient condition. There remains an unmet need for a medical device system capable of monitoring THC in a clinically meaningful way, particularly in an implantable device that enables ambulatory THC monitoring.

THC monitoring can provide useful information in a wide range of patient monitoring applications in which disease states or conditions are associated with tissue ischemia, tissue hypoxia, or blood pathologies. THC can vary as a result of changes or deficiencies in central cardiac function, local vascular function, central respiratory function, central or local nervous system function, or local metabolic changes in the tissue being monitored. The wide range of conditions that may benefit from the ability to monitor THC in clinically meaningful, calibrated units, includes monitoring applications that are acute, e.g. one day or less, as well as chronic, e.g. more than one day, weeks, months or even years.

FIG. 1 is a schematic view (not drawn to scale) of an implantable medical device system 2 in which methods described herein for monitoring THC in a patient may be usefully practiced. System 2 is shown to include an IMD 10 operating in conjunction with one or more optical sensors 12, 20, 30, 34, and/or 40. In this illustrative embodiment, (IMD) 10 is shown as a cardiac pacemaker coupled to leads 17 carrying electrodes 16, 18 and 19 extending into the patient's heart 8. IMD 10 may be configured to deliver cardiac pacing therapy for treating heart failure. In other embodiments, IMD 10 may take the form of any of a number of implantable medical devices, including, but not limited to, an implantable cardioverter defibrillator (ICD), a nerve stimulator, a cardiac assist device, or a fluid delivery pump capable, each of which may be configured for monitoring a patient condition and delivering a therapy automatically as needed.

In alternative embodiments, IMD 10 may be provided as a monitoring device for acquiring physiological diagnostic data without having therapy delivery capabilities. For example, IMD 10 may be a cardiac monitor, a respiration monitor, a syncope monitor, or any other type of monitor used to acquire data, including THC data, for diagnosing a patient condition and/or optimizing a medical therapy under the supervision of a clinician, such as prescribed medications.

In one embodiment, IMD 10 includes an optical sensor 12 incorporated along the hermetically-sealed housing 14 of IMD 10. IMD housing 14 encloses a battery and electronic circuitry or other components needed for performing device functions. Sensor 12 may alternatively be incorporated along IMD connector block 15. IMD connector block 15 is configured to receive one or more leads 17 and 22 to allow electrical connection of sensors or electrodes carried by leads 17, 22 to electronic components of IMD 10.

In some embodiments, an optical sensor 20 may be carried by a lead 22 extending from IMD 10. A lead-based sensor 20 may be used to allow deployment of sensor 20 at a tissue site remote from the implant site of IMD 10. Lead 22 may be tunneled extravascularly, e.g., subcutaneously or sub-muscularly, to a desired monitoring site.

In alternative embodiments, a lead 22 carrying a sensor 20, e.g. at a distal end of the lead 22, may be advanced within the vascular system and remain within a blood vessel for measuring THC in tissue adjacent to the blood vessel. Alternatively, lead 22 may be advanced intravascularly to a desired tissue site then advanced through the vessel wall, for example by puncturing the vessel wall, for placement at an adjacent tissue site.

System 2 may additionally or alternatively include an optical sensor 30 embodied as an implantable wireless optical sensor. Sensor 30 includes a power supply and circuitry housed in a hermetically sealed housing for performing THC measurements and further includes a telemetry module (not explicitly shown) enabling sensor 30 for wireless communication with IMD 10 or an external medical device 32. External medical device 32 may be a bedside monitor, a patient home monitor or a device programmer used to program IMD 10 and/or sensor 30 and retrieve data from the implanted devices.

A wireless sensor 30 may be implanted at a desired monitoring site remote from IMD 10 without the surgical constraints imposed by tethering sensor 30 to IMD 10 using a conductive lead. Wireless sensor 30 is shown implanted in an upper limb of patient 4, however a wireless sensor 30 may be positioned along any peripheral or core body site for monitoring a desired tissue volume, such as muscle, nerve including brain or spinal cord, cardiac, lung, or other body tissue. A wireless sensor 30 may be implanted for monitoring purposes only, without therapy delivery capabilities, and may be used alone to acquire THC data for transmission to external device 32 or in conjunction with IMD 10 for monitoring THC in patient 4.

System 2 may include an external, wireless optical sensor 40 for ambulatory, chronic or acute monitoring of THC. Sensor 40 emits light through the skin of the patient to obtain light attenuation measurements associated with the absorption and scattering of light by a tissue volume. External wireless optical sensor 40 is shown positioned along a lower limb of patient 4 but may be positioned along any peripheral or core body location, e.g. as listed above, for monitoring tissue oxygenation in a desired tissue volume. External sensor 40 may be held in a stable position using an adhesive patch or tape or using a securable band or cuff. External wireless optical sensor 40 includes a power supply and circuitry for performing THC measurements and telemetry circuitry enabling wireless communication between sensor 40 and IMD 10. Alternatively, optical sensor 40 may be configured for wireless communication with external medical device 32.

IMD system 2 may include an external sensor 34 in wired communication with a monitor 36 for monitoring THC transcutaneously. External sensor 34 and monitor 36 may be used in a patient's home, in a clinic, emergency room, or in a surgical theater for monitoring THC for periodic patient follow-up or during a clinical or surgical procedure, such as implantation of IMD 10 or optical sensors 20, 30.

The sensors described herein relate generally to a "reflection" mode of operation wherein the light emitting and light detecting portions of the sensor are in a substantially side-by-side arrangement and detected light is scattered by the tissue back to the detection portion. It is contemplated that an optical sensor may be configured to operate in a "transmission" mode, wherein the light emitting and light detecting portions of the sensor are arranged in facing opposition to each other. Detected light is light that is transmitted through the tissue. Furthermore, it is contemplated that in transmission mode configurations, one of the light emitting portion and the light detecting portion can be positioned externally against the skin "looking in" and the other can be positioned subcutaneously or submuscularly, "looking out" in facing opposition with the external portion.

As will be further described below, a medical device system 2 including an optical sensor for monitoring THC will include a processor for computing THC. In one embodiment, absolute $O_2Sat$ and calibrated THC measurements are computed from a sensor output signal and previously determined, empirically-derived values stored in memory, e.g. in the form of a look-up table. A processor and associated memory and other signal conditioning modules for performing THC measurement computations from raw optical sensor signals may be included in or distributed across any of the components shown in system 2, including external device 32, IMD 10, wireless sensors 30 or 40, lead-based sensor 20, or monitor 36.

External device 32 is shown in communication with a networked patient monitoring database 38. THC data may be transmitted to a monitoring database 38 to allow a clinician to monitor patient 4 remotely using a centralized Internet website or networked computer system. An example of a remote patient management system in which THC monitoring may be incorporated for managing patients is generally described in U.S. Pat. No. 6,599,250 (Webb, et al.), hereby incorporated herein by reference in its entirety.

As indicated above, monitoring of THC may be implemented in a wide range of patient monitoring applications associated with any condition associated with tissue ischemia or hypoxia. Such conditions may affect the brain, muscular tissue, heart or other vital organs. It is understood that THC monitoring may be performed in numerous body locations as needed for a particular monitoring application and that a medical device system employing THC monitoring methods described herein does not necessarily require all of the components shown in FIG. 1. The components shown are meant to illustrate various embodiments of one or more implanted and/or external devices which may include an optical sensor for obtaining THC measurements at a desired body location.

FIG. 2 is a top schematic view of an optical sensing device 100 for measuring THC according to one embodiment. Device 100 includes two optical sensors 102 and 102', which may be provided with substantially identical light emitting and light detecting components. Specifically, sensors 102 and 102' each include respective light sources 106 and 106' emitting light through respective emitting windows 114 and 114' and light detectors 108 and 108' receiving light through respective windows 116, 116'. Windows 114, 114', 116 and 116' are formed in the device housing 101, which may correspond to a housing of a dedicated sensor such as sensors 20, 30, 34 or 40 in FIG. 1 or an IMD housing 14. The functionality of each sensor 102 and 102' may be selectable such that one light source 106 or 106' emits light that is detected by both light detectors 108 and 108'. Alternatively, one detector 108 or 108' receives remitted light from light sources 106 and 106' operating in a time or frequency multiplexed manner.

In one embodiment, the attenuation of four wavelengths in the red to infrared spectrum is measured for obtaining $O_2Sat$ and THC measurements. The second derivative of a selected intermediate wavelength is scaled by another computed second derivative to obtain a light attenuation measurement dependent on the oxygenated state of chromophores present in the measurement volume and independent of the size of the measurement volume. The measurement of light attenuation for at least four different wavelengths allows a calibrated absolute $O_2Sat$ measurement to be obtained as described in U.S. patent application Ser. No. 12/771,322, hereby incorporated herein by reference in its entirety.

For example, light sources 106 may include four LEDs in emitting portion 102 for emitting light at separate wavelengths of 680 nm, 720 nm, 760 nm, and 800 nm. Alternatively, four LEDs provided as light sources 106 may emit light at 660 nm, 720 nm, 760 nm, and 810 nm. In another embodiment, four LEDs are included for emitting light at 720 nm, 760 nm, 810 nm, and 850 nm. In yet another embodiment, four LEDs are included that emit light at 720 nm, 760 nm, 810 nm, and 890 nm. Any combination of light sources emitting light at any of the wavelengths mentioned herein may be used. Furthermore, it is recognized that the specified wavelengths are approximate and each light source may emit a narrow band of light wavelengths which is approximately centered on, or at least includes, the specified wavelength. The light sources may be controlled to emit light sequentially or simultaneously.

The attenuation of the remitted light received by light detectors 108 or 108' is measured at four wavelengths. In the example of using measurements at 680 nm, 720 nm, 760 nm, and 800 nm, the second derivatives of the attenuation spectra at 720 nm and 760 nm are computed. The second derivative at 720 nm is scaled by the second derivative at 760 nm to obtain an oxygen-dependent, volume-independent measure of $O_2Sat$. The second derivative of light attenuation at 760 nm is dependent on the total hemoglobin concentration present in the tissue and the oxygenated state of the total hemoglobin present. As will be described in detail below, the second derivative of the attenuation measured at 760 nm is used to compute THC.

By arranging the light sources 106 and 106' and the light detectors 108 and 108' in a particular spatial manner with respect to one another, at least two different separation distances exist between one light source 106 or 106' and the two light detectors 108 and 108', or between one of the detectors 108 or 108' and the two light sources 106 and 106'. To illustrate, if light source 106' is enabled to emit light, the light detectors 108 and 108' are positioned at two distinct separation distances 104 and 105, respectively, from the light source 106'. Remitted light is received by light detectors 108 and 108' along two different paths shown schematically by arrows 110 and 112. The distance between the emitting and detecting portions of the sensor determines, in part, the optical pathway of the sensor and thus the measurement volume and depth in the tissue of interest.

The attenuation of remitted light at the spectral peak at 760 nm will be influenced by the absorption of light by hemoglobin in the measurement volume of tissue and the scattering of light by the tissue. As such, in order to obtain a calibrated measurement of THC from a light attenuation measurement, the measurement is corrected for artifact due to scattering of light by the tissue. The optical properties of the tissue, however, are generally unknown and can change over time. In order to correct a light attenuation measurement for scattering artifact, the tissue scattering coefficient, $\mu_s'$, needs to be determined.

In one embodiment, attenuation measurements taken at two different separation distances allow $\mu_s'$ to be estimated from empirically-derived equations or look-up tables. For example, two separation distances 104 and 105 from light source 106' may be used to obtain two attenuation measurements at two different light detectors 108 and 108'. Current methods for computing the light absorption and scattering properties of a material using spatially resolved reflectometry involve iterative, computationally intensive and time consuming processes that would not be highly practical in an implantable or real-time acute medical device application. A method for determining discrete values of $\mu_s'$ a priori using, e.g., Monte Carlo simulations or tissue phantoms having known properties, or a combination of both, provides accurate $\mu_s'$ estimation for use in real-time monitoring in an acute or chronically implantable device. The a priori data is used to solve for best fit equations or to establish a look-up table of discrete $\mu_s'$ values.

As will be described further below, during sensor operation, the light distribution measured at two different emitting-to-detecting separation distances, e.g., distances 104 and 105, and the calibrated equation or look-up table is used to solve for $\mu_s'$. As shown in FIG. 2, different separation distances required for $\mu_s'$ estimation, according to some embodiments, can be used when multiple light sources and light detectors are available. In other embodiments, attenuation at a single separation distance may be used with additional constraints placed an $\mu_a$ to allow for a solution for $\mu_s'$ to be obtained.

Remitted light measured by light detectors 108 and 108' along paths 110 and 112, respectively, will be attenuated due to both light absorption and light scattering by the tissue measurement volume. In order to obtain a calibrated THC measurement in clinically meaningful units, the attenuated light measured by device 100 is corrected for light scattering artifact. The arrangement shown in FIG. 2 is merely one example of many possible arrangements to obtain light attenuation measurements at one or more separation distances between a combination of one or more light sources and one or more light detectors that enables estimation of $\mu_s'$ for using scattering artifact correction.

Figure 2A:
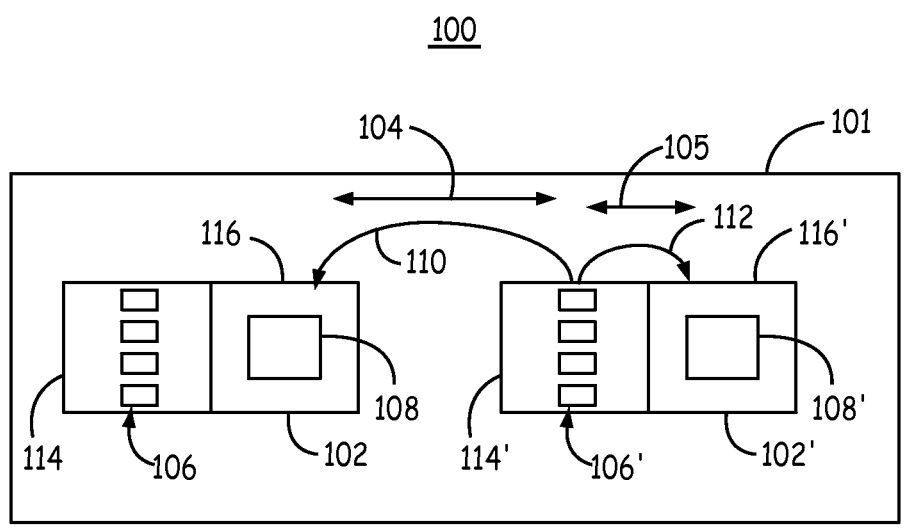
FIGS. 2A through 2D are top schematic views of different optical sensing device configurations that can be used for measuring THC.
Figure 2B:
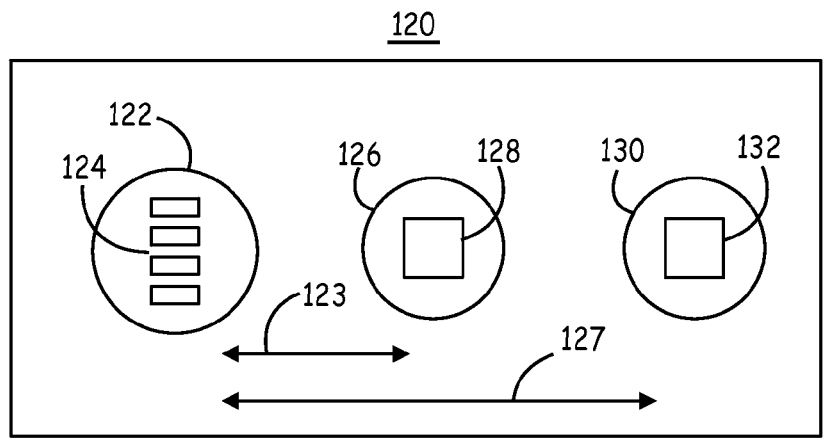
Figure 2C:
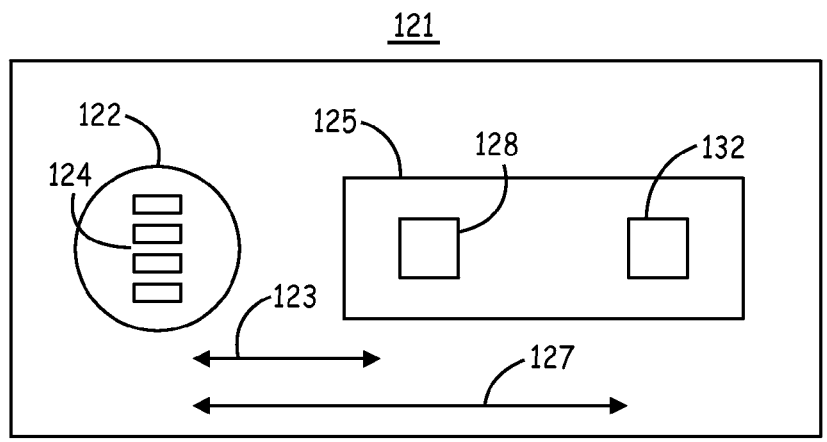
Figure 2D:
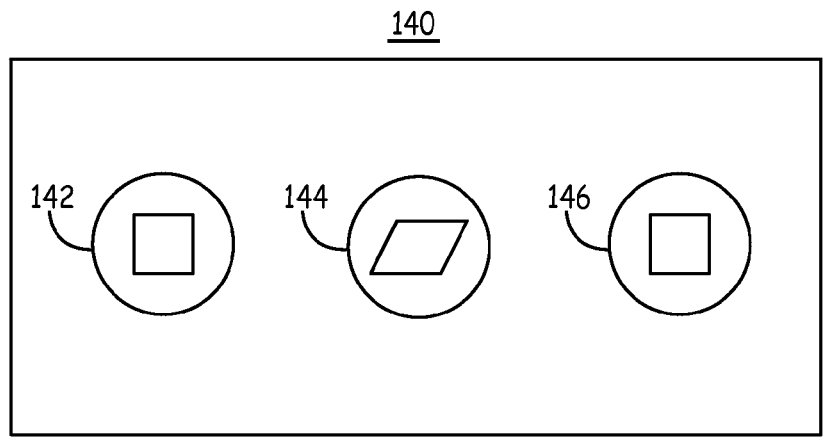

Other possible arrangements of light sources and light detectors for obtaining attenuation measurements at one or more different separation distances are shown in FIGS. 2B through 2D. In FIG. 2B, an optical sensor 120 includes a light source 124 positioned to emit light through one window 122, and light detectors 128 and 132 positioned to detect light through two separate windows 126 and 130 located at two different separation distances 123 and 127 from the light source 124.

Alternatively as shown in FIG. 2C, the two light detecting devices 128 and 132 could be positioned at two different distances 123 and 127 from the light source 124 to detect light through a single common window 125. It is further contemplated that one light detector could be positioned to detect light emitted by two light emitters located at two different separation distances from the light detector but emitting light through a single common window. For example, vertical cavity surface emitting lasers (VCSELs) could emit light through a common window and be positioned at two different distances (one nearer and one further) from a photodiode window. When a single light detector is used in combination with two light sources to obtain measurements at two separation distances, the emitted light signals are controlled in a time or frequency multiplexed manner to allow separate light attenuation measurements to be obtained for the two separation distances.

The light detectors in any of the sensor embodiments described herein may be embodied as photodiodes. Other components suitable for use as a light detector include a photoresistor, phototransistor, photovoltaic cell, photomultiplier tube, bolometer, charge-coupled device (CCD) or an LED reverse-biased to function as a photodiode.

The light sources, also referred to herein as light "emitters", in any of the sensor configurations described herein may be embodied as a single white light source or multiple light sources emitting light at separate spaced-apart wavelengths. Suitable light sources include, without limitation, optoelectronic devices such as light emitting diodes (LEDs), lasers such as VCSELs, luminescent, phosphorescent and incandescent light sources. The light source 124 in FIGS. 2B and 2C is shown as four LEDs emitting light at four separate wavelengths, such as the wavelengths listed above.

In FIG. 2D, an alternative embodiment of an optical sensor 140 is shown including a light source 144, such as VCSELs, emitting collimated light, oriented non-normal to the tissue, with two light detectors 142 and 146 located equidistant from the light source 144, on either side of the light source. In this approach, asymmetry in the light attenuation measured by the light detectors 142 and 146 is influenced by the optical properties of the adjacent tissue. The two different light attenuation measurements can be used to determine the influence of tissue scattering properties and thus correct a measurement of light attenuation for tissue scattering artifact.

Embodiments of an optical sensor shown here in include multiple light emitting and/or detecting components. As will be further described below, some methods for measuring μs' require attenuation measurements taken at a single separation distance. As such, an optical sensor useful for practicing methods described herein may include a single emitting portion and a single detecting portion for obtaining attenuation measurements.

Figure 3:
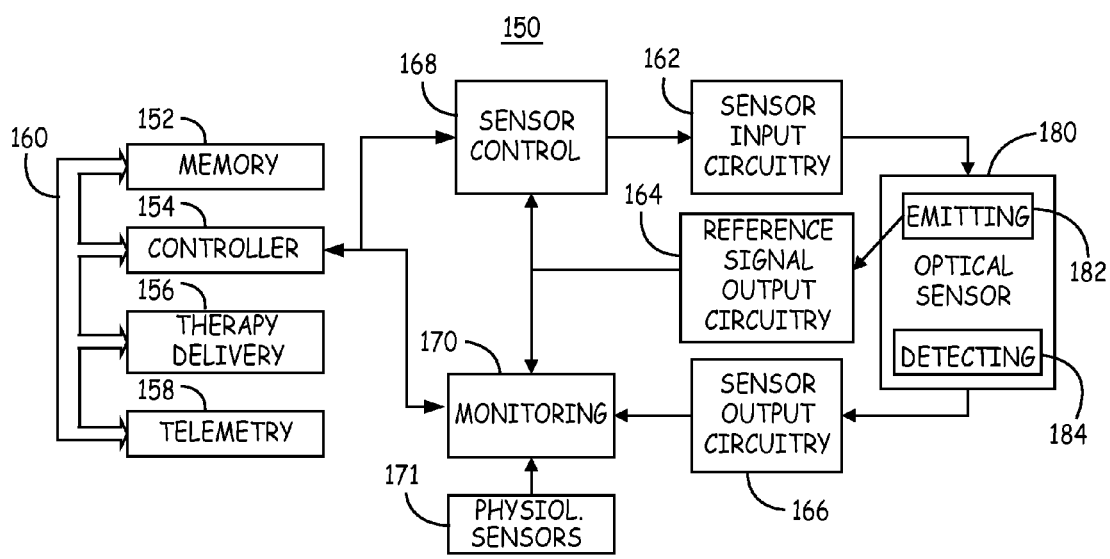
FIG. 3 is a functional block diagram of an optical sensing device which can be used for measuring THC.

FIG. 3 is a functional block diagram of a medical device 150 that can be used for measuring THC. The functionality described in conjunction with FIG. 3 may be implemented in or distributed across any of the medical device system components shown in FIG. 1. For example, the functionality shown in FIG. 3 may be fully implemented in IMD 10, or may be implemented in IMD 10 in conjunction with implantable lead-based sensor 20, implantable wireless sensor 30, external wireless sensor 40, external wired sensor 34, external device 32, external monitor 36, or any combination thereof (all shown in FIG. 1).

Device 150 includes an optical sensor 180, which may be positioned along a hermetically sealed housing of a device or carried by a lead. Sensor 180 may correspond to any of the sensor embodiments described herein or as shown in FIGS. 2A through 2D. Device 150 further includes sensor input circuitry 162, sensor output circuitry 166, and optionally includes reference signal output circuitry 164 when a reference light detector is included in the optical sensor 180 for measuring the intensity of emitted light.

Optical sensor 180 generally includes a light source for emitting light through a blood perfused tissue of the patient and a light detector for generating a signal representative of an intensity of light scattered by the blood perfused tissue to the light detector. The light passed through the tissue (including blood) may be selected to include four or more wavelengths for use in computing a volume-independent measure of $O_2Sat$, from which an absolute, calibrated tissue $O_2Sat$ may be derived, as well as a measurement of THC. Typically, the intensity of scattered light falling in the red part of the visible light spectrum and the infrared (IR) portion of the light spectrum is measured.

Sensor input circuitry 162 is coupled to a light emitting portion 182 of optical sensor 180. Light emitting portion 182 includes one or more light sources for emitting light that includes at least four different wavelengths for computing calibrated tissue oxygenation measurements. Sensor input circuitry 162 provides input signals to the optical sensor 180.

In particular, sensor input circuitry 162 provides the drive signals applied to the light source(s) included in light emitting portion 182 to cause controlled light emission, e.g. controlled intensity, time duration and frequency.

Sensor input circuitry 162 is controlled by sensor control module 168 which coordinates the beginning time, duration, and frequency of drive signals produced by sensor input circuitry 162. Control signals may include a period of no light emission for ambient light measurement. Drive signals may be applied to individual light sources simultaneously to cause "mixed" light emission from all light sources. Light emission from two or more light emitting portions may be controlled in a time or frequency multiplexed manner to allow light absorbance spectra to be measured for two different separation distances by a single light detector.

Sensor output circuitry 166 receives the light detector signal from light detecting portion 184 and demodulates, digitizes, filters or performs other appropriate signal conditioning to provide a digital output signal to monitoring module 170. Sensor output circuitry 166 may include an analog-to-digital converter and memory for digitizing an analog output signal from detecting portion 184, providing the digitized signal to monitoring module 170, storing measurement results for future retrieval as well as storing calibration coefficients.

In one embodiment, monitoring module 170 includes processing circuitry that uses the optical signal to compute a volume-independent measurement of $O_2Sat$ and a calibrated measurement of THC using the intensities of the multiple wavelengths measured by detecting portion 184. Monitoring module 170 may detect physiological events or conditions using $O_2Sat$ and THC and optionally from additional physiological sensors 171.

As used herein, a "volume-independent" measure of oxygen saturation refers to a measurement that is substantially independent of the size of the optical sensor path that encompasses a measurement volume within a substantially uniform tissue. In other words, in a substantially uniform, homogenous tissue, a longer optical pathway that encompasses a larger measurement volume and a relatively shorter optical pathway that encompasses a smaller measurement volume within the same uniform tissue will produce substantially equal $O_2Sat$ measurements. A volume-dependent measure of oxygen saturation would be dependent on oxygen and the measurement volume and would thus produce two different measurements for two different measurement volumes in the same uniform, homogenous tissue. The second derivative method for computing $O_2Sat$ as described in the above-incorporated '322 patent application eliminates scattering effects of a changing measurement volume and provides a volume-independent measurement of $O_2Sat$.

A homogenous tissue is a tissue that includes structures that are relatively small compared to the measurement volume. For example, if measurement volume is related to emitting-to-detecting spacing, a homogenous tissue might be a tissue wherein tissue structures or features have a dimension of approximately 1/10 of the emitting-to-detecting spacing or less. A uniform tissue is a tissue that has uniform oxygenation through the depth of the measurement volume in contrast to an oxygenation gradient. If a tissue is non-uniform or non-homogeneous, different oxygen saturation measurements will be obtained depending on the optical path of the sensor. As will be further described below, two different $O_2Sat$ measurements obtained by two different separation distances may indicate non-homogenous tissue and may be used in selecting how a THC measurement is taken or used.

A calibrated, absolute $O_2Sat$ and a calibrated THC are derived from the light detector output signal by monitoring module 170 and provided to a device controller 154 (which may include a processor, state machine or other control circuitry) for monitoring tissue oxygenation and controlling device-delivered therapy.

Device 150 includes a therapy delivery module 156. The monitored $O_2$Sat and THC may be used in determining when a therapy is needed and in controlling therapy delivery or adjustments thereto based on events or conditions detected by monitoring module 170. Therapy delivery module 156 may include electrical pulse generation capabilities for delivering cardiac pacing pulses, cardioversion/defibrillation shocks, or nerve stimulation therapies. Therapy delivery module 156 may additionally or alternatively include a fluid delivery pump for delivering a pharmaceutical or biological fluid to the patient, such as cardiac drugs or other therapeutic fluids.

Device 150 may include other sensors 171 for sensing physiological signals such as ECG or cardiac EGM signals, blood pressure, patient activity, patient posture, heart sounds, temperature, or the like. Such sensor signals may be used in combination with the monitored $O_2$Sat and THC for detecting a patient condition.

Data acquired by processor 154 relating to THC may be stored in memory 152 and/or transferred to a medical device programmer, home monitor, computer, or other external or bedside medical device via wireless telemetry module 158 for display and/or review by a clinician. Data relating to $O_2$Sat and THC may also be transmitted to another implantable or external medical device for use in controlling a device delivered therapy. Processor 154 transmits data to and from memory 152, therapy delivery module 156, and telemetry module 158 via data/address bus 160.

Figure 4:
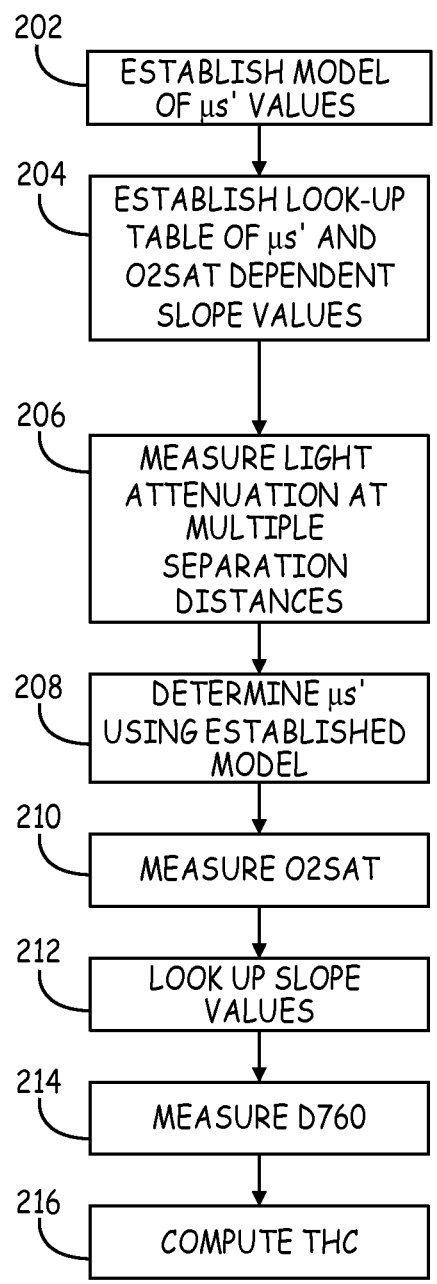
FIG. 4 is a flow chart of one method for monitoring THC.

FIG. 4 is a flow chart 200 of one method for monitoring THC. Flow chart 200 and other flow charts presented herein are intended to illustrate the functional operation of the device, and should not be construed as reflective of a specific form of software or hardware necessary to practice the methods described. It is believed that the particular form of software will be determined primarily by the particular system architecture employed in the device and by the particular detection and therapy delivery methodologies employed by the device. Providing software to accomplish the described functionality in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Measurement of attenuation of light at an appropriate spectral peak, e.g. at 760 nm, provides a measurement correlated to light absorbance due to hemoglobin concentration in a tissue volume. The light absorbance will be influenced by the oxygenated state of the total hemoglobin present in the tissue and will thus have dependency on $O_2$Sat. As discussed above, in addition to the effects of absorbed light, the measured light attenuation will further include artifact due to light scattering by the tissue. The light scattering will vary based on the optical properties, i.e. tissue scattering coefficient $\mu_s'$ and tissue absorbance coefficient $\mu_a$, of the particular tissue being monitored. An equation provided to compute THC from a measurement of light attenuation at 760 nm, therefore, will include a term to correct for light scattering by the tissue and a term to account for the oxygenated state of the hemoglobin present.

In order to determine these $\mu_s'$- and $O_2$Sat-dependent terms, empirically-derived mathematical models of these terms are stored in the form of a look up table or in the form of mathematical equations which can be solved to obtain a value of the $\mu_s'$-dependent term and the $O_2$Sat-dependent term. In order to establish a value of $\mu_s'$ for computing the $\mu_s'$-dependent term, an additional empirically-derived look-up table or mathematical equation is stored for obtaining a value of $\mu_s'$ corresponding to light attenuation measurements acquired at two different separation distances.

As such, at block 202, a mathematical model of equations or look-up table of values for a tissue scattering coefficient $\mu_s'$ is established. The equations allow $\mu_s'$ to be solved for using light attenuation measurements taken at one or more separation distances during THS monitoring. The look-up table will provide a $\mu_s'$ value for known light attenuation measurements. The mathematical model is generated using empirically measured values of light attenuation over a range of known $\mu_s'$ and $\mu_a$ values, as will be described in detail below, for example in conjunction with FIGS. 5 and 6.

At block 204, a look-up table of values or equations for $\mu_s'$- and $O_2$Sat-dependent slope terms used in an equation for computing THC is established at block 204 for given values of $\mu_s'$ and $O_2$Sat. Methods for establishing an equation or look-up table of values for $\mu_s'$-dependent and $O_2$Sat-dependent slope terms in a THC equation will be described below in conjunction with FIG. 8.

At block 206, light attenuation is measured at two or more separation distances. Alternatively, light attenuation is measured at two equal separation distances using a non-normal collimated light source (e.g. a VCSEL). The light attenuation at two different separation distances (or at two asymmetric angles resulting from a non-normal incident light source) allows a value for $\mu_s'$ to be solved for at block 208 using the mathematical model established for $\mu_s'$ at block 202.

At block 210, $O_2$Sat is measured. Knowing the measured $O_2$Sat and the estimated $\mu_s'$ from block 208, the $\mu_s'$- and $O_2$Sat-dependent slope terms determined at block 212, using stored look-up tables or stored equations for computing these terms. At block 214, the second derivative of light attenuation at a wavelength of 760 nm (D760) is determined at one or both of the separation distances. THC is then computed at block 216 using the measured D760 and the $\mu_s'$- and $O_2$Sat-dependent slope terms.

An external device or computer processor may perform the processes at blocks 202 and 204 for generating look-up tables or best fit equations that are then stored for later use in computing THC during patient monitoring. The look-up tables and/or equations may be programmed into an implantable medical device or sensor for computing THC from light attenuation measurements. The THC measurements may be transferred to another internal or external device or used directly by the device computing THC. Alternatively, raw light attenuation data may be transferred to an external device storing the look-up tables and/or equations for processing into THC measurements.

Figure 5:
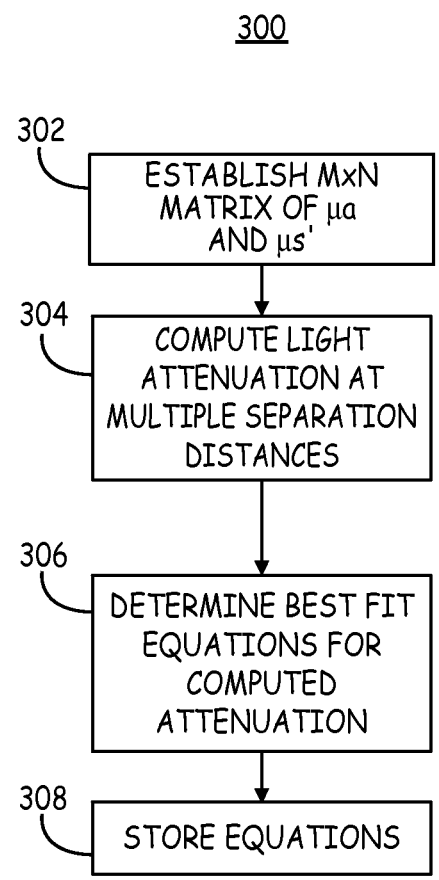
FIG. 5 is a flowchart of one method for empirically obtaining a mathematical model for estimating a coefficient of tissue scattering ($\mu s'$).

FIG. 5 is a flowchart 300 of one method for empirically obtaining a mathematical model for estimating $\mu_s'$. At block 302, an M×N matrix is established defining a range of possible $\mu_a$ and $\mu_s'$. For example, $\mu_a=(0.01\ 0.1\ 1.0\ 10\ 100)$ 1/mm and $\mu_s'=(0.01\ 0.1\ 1.0\ 10\ 100)$ 1/mm. The M×N matrix is generated automatically by a processor in the medical device system or the processor is configured to receive a user-entered range of coefficients. The M×N matrix of $\mu_a$ and $\mu_s'$ values is used to compute an M×N matrix of Monte Carlo solutions of the light attenuation for two different separation distances.

The net tissue attenuation is calculated for each possible pair of µa and µs' for two or more separation distances, d, of the light source and the light detector at block 304. The separation distances between the light source and light detectors (or incident angle of the light source if applicable), the radius of the light source, and optical properties of the sensor are provided as input for the Monte Carlo solution. Optical properties of the sensor include the surface absorptance and surface scattering at tissue/sensor interface and optical properties of the windows and cavities surrounding the light sources and the light detector(s). The computed attenuation may be normalized by the power of the light source.

At block 306, a best fit equation is determined for defining a mathematical model correlated to the computed attenuation matrix. An empirical formula of the form µa=f(A, µs') is found for each set of data corresponding to the two different separation distances and obtained from the Monte Carlo simulation. This results in two sets of fit coefficients, one for A1, and another for A2. The two best fit equations can be denoted as µa=f1(A1, µs') and µa=f2(A2, µs'), respectively, wherein A1 is the attenuation computed for the M×N matrix of µa and µs' values at a first separation distance and A2 is the attenuation computed for the same M×N matrix for the second separation distance.

The equations are stored at block 308 and are used for computing actual µs' in a reverse solution using two measurements of light attenuation at two different separation distances during sensor operation.

The form of the best equations may vary between embodiments. In one embodiment, the following equation is used as a semi-empirical model in which coefficients are solved for to determine the best fit equations to the computed Monte Carlo solutions for A1 and A2.

$$\mu_a = \frac{\sum_{i=0}^{L}\sum_{j=0}^{M} C_{ij}(\mu'_s)A^j}{\sum_{k=0}^{N} D_k(\mu'_s)^k} \quad \{1\}$$

Figure 7:
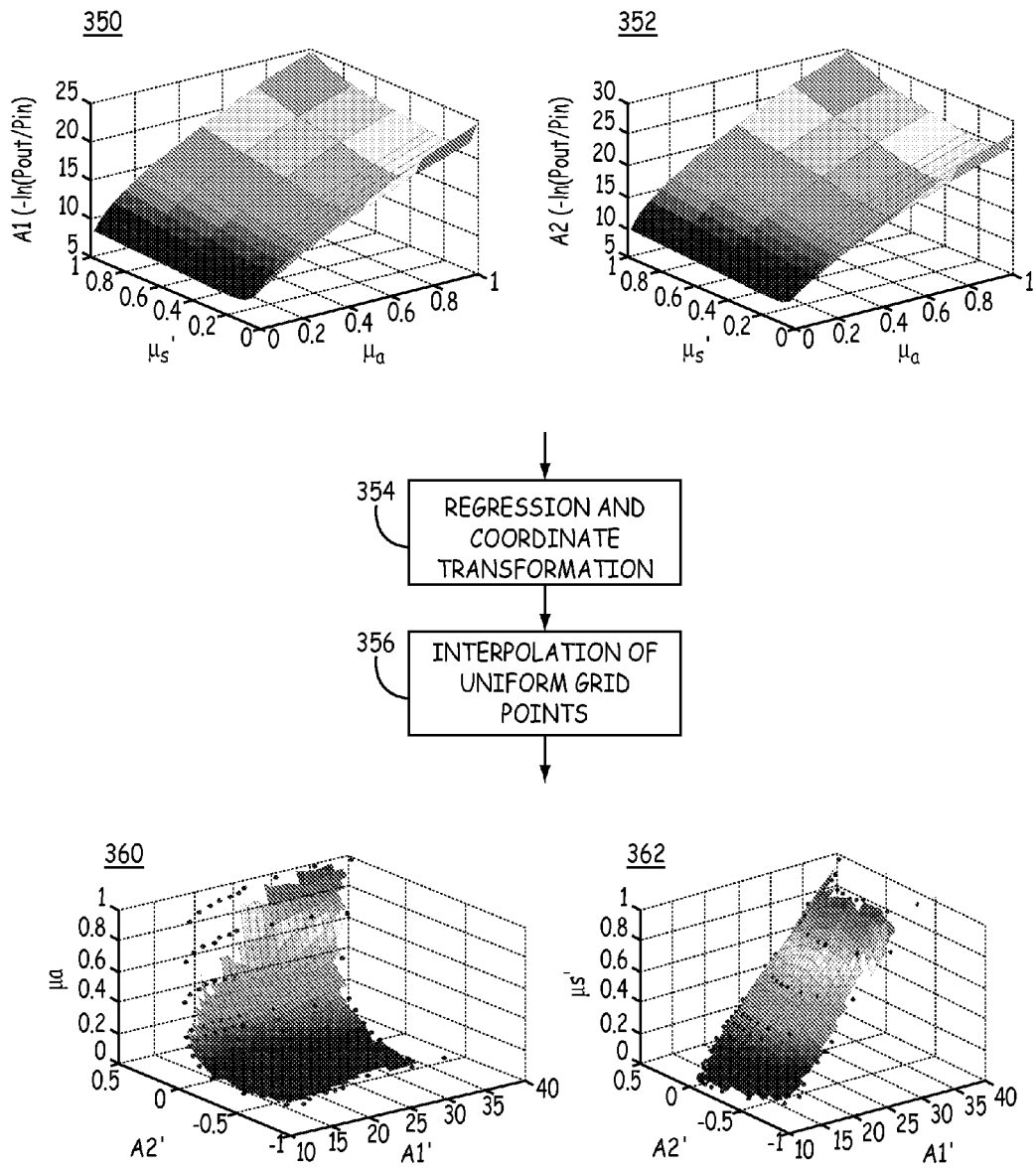
FIG. 7 is a set of plots of the results of mathematically modeling attenuation A over selected ranges of $\mu s'$ and a tissue absorption coefficient $\mu a$

In Eqn. 1, C and D are coefficients that are solved for in the best fit computations and A is attenuation computed by the Monte Carlo solution. FIG. 7 illustrates a plot 350 of a three-dimensional surface of attenuation A1 computed for a first separation distance using a Monte Carlo solution over a range of µa and µs' values. A second plot 352 shows the three-dimensional surface of attenuation A2 computed for a second separation distance using the Monte Carlo solution over the same ranges of µa and µs' values. Eqn. 1 above provides one form of a best fit equation that may be determined to match the plotted surfaces, where C and D are solved for using the values of µa, µs' and A1 or A2 for obtaining the two equations in the general form of µa=f1(A1, µs') and µa=f2(A2, µs').

Figure 6:
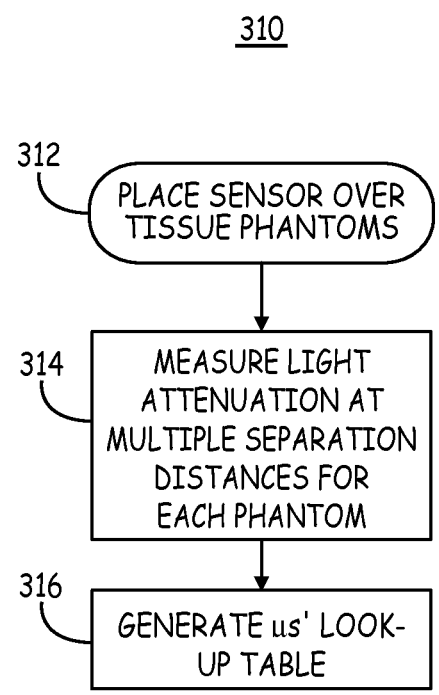
FIG. 6 is a flow chart of one alternative method for estimating $\mu s'$ for use in computing THC during tissue monitoring.

FIG. 6 is a flow chart 310 of an alternative method for establishing a look-up table of µs' values (or empirically-derived equations) for determining µs' from A1 and A2 measurements during tissue monitoring. At block 312, the optical sensor is placed over a phantom tissue sample having known light absorption and light scattering properties. The tissue phantom is selected to have light absorption and scattering properties corresponding to a range of an M×N matrix of µa and µs'. Multiple tissue phantoms may be used having varying optical properties or the optical properties of a tissue phantom can be varied during measurements. A medical device system processor configured to compute a mathematical model of light attenuation as a function of µs' is configured to receive the known values of µa and µs' corresponding to a tissue phantom(s) as the optical properties of the tissue phantom are varied.

At block 314, the light attenuation is measured by the sensor at multiple separation distances between light source(s) and light detector(s) for varying µs' of the tissue phantom. A µs' look-up table may be generated from the light attenuation measurements and the known µs'. Linear interpolations may be used to obtain A1 and A2 values for a given µs' to generate a look-up table providing a µs' estimation for equally spaced A1 and A2 values. The look-up table of values is stored in an IMD (or other system component) such that for a measured light attenuation at a distance d1, and a simultaneously or sequentially measured light attenuation at a second distance d2, the value of µs' may be found in the look-up table and subsequently used to compute a THC.

Alternatively, best fit equations are determined to define µs' as a function of the measurements of light attenuation as described above. An inverse solution of the best fit equation for the empirically derived data sets for A1 and A2 may be determined to define µs' as a function of A1 and A2 over the range of tabulated empirical measurements.

In summary, either a matrix of mathematical solutions for A1 and A2 determined using a range of known µa and µs' values, or empirically measured A1 and A2 for known µa and µs' values in controlled tissue phantoms, or a combination of both may be used to generate a mathematical model for determining µs' from measured values of A1 and A2 during tissue monitoring. The mathematical model may be either a set of stored equations used to solve for µs' given the measured A1 and A2 spectra or a table of look-up values of µs' given the measured A1 and A2.

FIG. 7 is a set of plots of the results of mathematically modeling attenuation A over selected ranges of µs' and µa. In plot 350, attenuation A1 is modeled for a separation distance of 10 mm, and in plot 352 attenuation A2 is modeled for a separation distance of 13 mm. Other separation distances could be used. This model was generated using a Monte Carol solution. A similar model could be plotted using actual attenuation measurements performed in tissue phantoms at two different separation distances.

Plots 350 and 352 are generated a priori using a Monte Carlo solution or tissue phantoms having known ranges of µs' and µa for determining A1 and A2. The data of plots 350 and 352 needs to be inverted in order to provide a look-up table or derive best fit equations for determining µs' when µs' is the unknown and tissue attenuation measurements are made by an optical sensor for THC monitoring. In order to obtain the inverted data, the data shown in plots 350 and 352 are replotted to produce µa plotted as a function of A1 and A2 (plot 360) and µs' plotted as a function of A1 and A2 (plot 362). In this way, given two attenuation measurements A1 and A2 acquired during patient monitoring, the values for µa and µs' can be extracted or interpolated from the plots 360 and 362.

A simple data inversion will likely yield a plot area in which the principle components of A1 and A2 are not aligned with orthogonal axes of the plot area. The grid of the A1 and A2 values may also be highly irregular. In order to obtain a more useful form of the plotted data as shown in the plots 360 and 362, additional steps are taken in the inversion process as shown by blocks 354 and 356 to align the principle directions of A1 and A2 with the orthogonal axes of the plot area and to create a uniform grid of the A1 and A2 values.

At block 354, a coordinate transformation is performed. A regression operation to determine the principle directions of the A1 and A2 axes allows the following coordinate transformation to be applied:

$$\begin{bmatrix} A1' \\ A2' \end{bmatrix} = \begin{bmatrix} \cos\theta & -\sin\theta \\ \sin\theta & \cos\theta \end{bmatrix} \begin{bmatrix} A1 \\ A2 - r \end{bmatrix}$$

wherein θ and r are transformation parameters determined by the regression analysis performed on the (A1, A2) values shown in plots 350 and 352. This provides a grid area having orthogonal axes aligned with the principle components of A1 and A2, referred to as A1' and A2'.

At block 356, an interpolation of μa and μs' points over a uniform grid of values for A1' and A2' is performed to generate plots 360 and 362 of μa and μs', respectively, over uniform grids of A1' and A2'. Original data points from plots 350 and 352 are shown as block dots. The data of plots 360 and 362 can be stored in the form of look-up tables or best-fit equations in an implantable device.

The generation of plots 360 and 362 requires considerable processing power and time but is done only once, a priori, by an external processor. The resulting mathematical model of μa and μs' for measured values of A1 and A2 in the form of a look-up table or coefficients for a set of best fit equations reduces the processing burden in the implantable device. The look-up table or best fit equations are stored in the memory of the implantable device allowing a computationally efficient method for determining μa and μs' from attenuation measurements obtained by the device.

Figure 8:
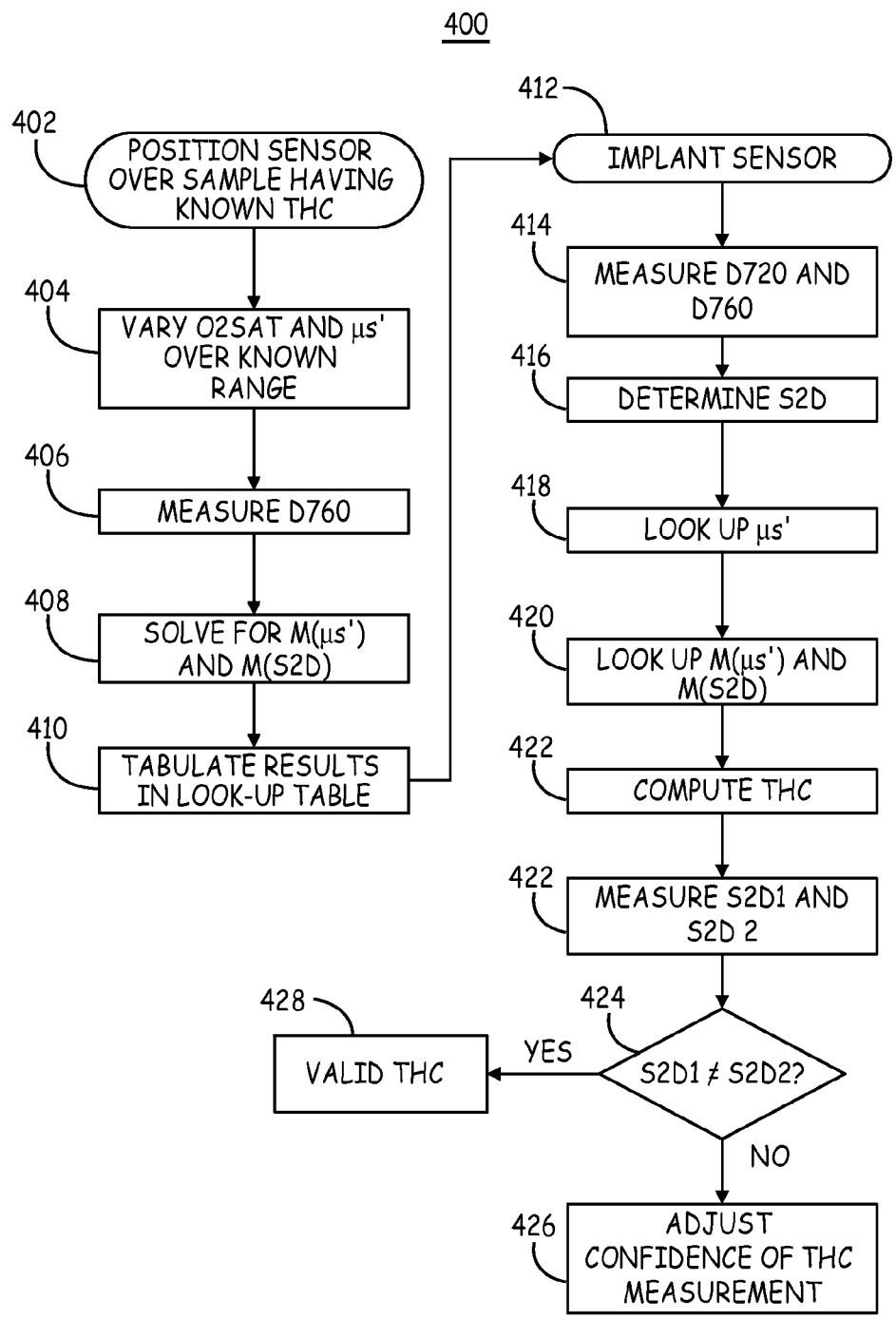
FIG. 8 is a flow chart of one method for measuring THC using an optical sensor.

FIG. 8 is a flow chart 400 of a method for measuring THC using an optical sensor. Initially, the optical sensor is calibrated using a sample having a known THC. The sensor is positioned over the sample at block 402. The $O_2$Sat and μs' of the sample is varied in a controlled manner to obtain light attenuation measurements over a range of known μs' and $O_2$Sat values for the known THC of the sample. One method for varying μs' and $O_2$Sat in a tissue phantom sample would be to mix a fat emulsion or microspheres with blood then change μs' by changing the size of microspheres or the scattering properties of the fat emulsion, e.g. by varying its concentration. In another method, a two layer flow cell is used having a tissue phantom material, such as polyethylene foam, with varying cell size to get varying scattering properties. The second layer is a thin (e.g., ~1 mm) layer of blood, which is provided with variable oxygenation. The layer of blood is positioned between the sensor and the tissue phantom.

For different known values of μs' and $O_2$Sat, the light attenuation is measured by the sensor to obtain the second derivative of the spectral peak at a selected wavelength. In one embodiment, the second derivative of light detected at a wavelength of 760 nm (D760) is computed from light attenuation spectra at three wavelengths, 760 nm and two adjacent wavelengths, e.g. 720 nm and 800 nm. Other spectral peaks may be used for successfully obtaining a THC measurement but possibly with reduced signal-to-noise ratio. THC can be given as a function of D760 by the following equation:

$$THC = \{(1/SF) \times (M(\mu s') \times M(S2D) \times D760)\} + w \quad \{2\}$$

wherein S2D is the scaled second derivative of the attenuation at 720 nm scaled by the second derivative of the attenuation at 760 nm expressed as $$S2D = D''(720)/D''(760) \quad \{3\}$$

This S2D(720) is dependent on oxygen saturation of the hemoglobin present in the measurement volume but independent of the size of the measurement volume.

M(μs') in equation {2} may be expressed as M(μs')=C1"μs'+C2, wherein C1 and C2 are calibration constants. Similarly M(S2D)=C3*S2D+C4, wherein C3 and C4 are calibration constants. Six calibration constants (C1, C2, C3, C4, SF and w) can be stored in place of a lookup table of values at block 410, particularly for applications where memory space is limited The μs'- and S2D-dependent terms may be solved for separately and tabulated individually in a look up table (or as equation constants) at block 410 for known values of μs', S2D and THC. Alternatively, a combined term (M(μs')×M(S2D)) may be solved for and tabulated for different combinations of known μs', S2D, and known THC at block 410.

SF in Eqn. 2 is a spacing factor that may be used if the light source and light detector are spaced at a different distance during calibration than after implantation. This term can be determined at calibration and may be omitted if the same sensor (or same separation distance) is used at calibration and in the implanted sensor. The term 'w' is a calibration constant determined at the time of calibration and stored in device memory. This calibration constant may also be stored as a function of μs' if higher fidelity measurements are required.

After establishing a look-up table of values (or best fit empirical equation constants for M(μs') and M(S2D) during the calibration procedure, an optical sensor may be positioned or implanted at block 412 for performing acute or chronic THC measurements. During sensor operation, the second derivatives of the light attenuation spectra are determined at block 414 for the intermediate wavelengths 720 and 760 nm. The S2D at 720 nm is computed at block 416. A method for measuring S2D using a four wavelength optical sensor of the measured light spectra is generally described in the above-incorporated patent application '322.

At block 418, the measured light attenuation at a selected wavelength (e.g. 760 nm) and known separation distance is used to compute or look up μs' using the stored equations or look-up table described in conjunction with FIG. 4 or 5. The light attenuation may be measured at a selected wavelength, e.g. 760 nm, or any combination of spectral peaks at two separation distances. When more than one wavelength is measured, the resulting μs' for each wavelength can be averaged. For example, two different light attenuation measurements at two different spacings or two different resulting angles of a non-normal incident light source may be measured at a single wavelength, e.g. 760 nm, and the μs' is determined for that wavelength using the A1 and A2 measurements and the equations or look-up table using the methods of FIG. 5 or 6. Alternatively, an average μs' may be computed using light distributions measured at the three wavelengths used to compute the second derivative of light attenuation at 760 nm (i.e., 760 nm and two adjacent wavelengths) for two separation distances.

Using the S2D measured at block 416 and μs' determined at block 418, the value(s) of M(μs') and M(S2D), individually or in a combined term, are found in the corresponding stored look-up table (or computed using stored constants C1, C2, C3 and C4 for an empirically-derived best fit equation) at block 420. Using the computed or look-up table value(s) for M(μs') and M(S2D), the stored calibration constant 'w', and D760 measured at block 414, THC can be computed at block 422 using the equation {2} shown above.

The D760 term measured at block 414 is computed as the second derivative of the light attenuation spectral peak at 760 nm, using the peaks at 720 nm and 800 nm or other neighboring spectral peaks for computing the second derivative as described in the '322 application. While light attenuation measurements at two separation distances are needed for this embodiment for determining µs' at block 418, either of the separation distances between the light source and light detector may be used for measuring the D760 term used to compute THC at block 422. In one embodiment, the larger separation distance is used to obtain D760 for computing a THC measurement averaged over a larger volume of tissue. In other embodiments, D760 may be computed for two or more separation distances and averaged to obtain the D760 term in Equation 2 above. In still other embodiments, a THC may be computed for each D760(and S2D) measured for each respective separation distance and then the two (or more) THC measurements may be averaged to obtain THC for the tissue of interest.

THC can be monitored periodically or on a triggered basis and may be compared to established thresholds and/or stored with historical data to determine short-term or long-term trends in THC for detecting and discriminating physiological conditions of the patient. Based at least in part on the THC measurement, a need for therapy delivery or therapy adjustment may be determined and performed accordingly as described in conjunction with FIG. 3.

An optional verification of the reliability of the THC measurement may be made at blocks 422 through 428. At block 422, a second S2D measurement is obtained at a second emitting-to-detecting separation distance different than the first S2D measurement. Since the S2D measurement is volume independent, different optical pathways should result in approximately equal S2D measurements in a homogenous tissue. If the two S2D measurements are approximately equal, the THC measurement is deemed valid at block 428.

If the two measurements are not approximately equal, as determined at block 424, there is an indication of non-homogenous tissue. Non-homogenous tissue may have varying optical properties such that a single established value of µs' does not accurately reflect the non-homogenous tissue properties. The confidence in the THC measurement using a single established µs' is therefore lowered. The THC measurement may be discarded or a weighting factor or other confidence indicator may be adjusted at block 426 to reduce the weight of the measured THC in an algorithm for detecting a physiological condition. THC values may be flagged as lower confidence values in a report or display. Alternatively, multiple THC measurements may be obtained at different separation distances and averaged in response to determining that the tissue may be non-homogeneous based on differing S2D measurements.

Figure 9:
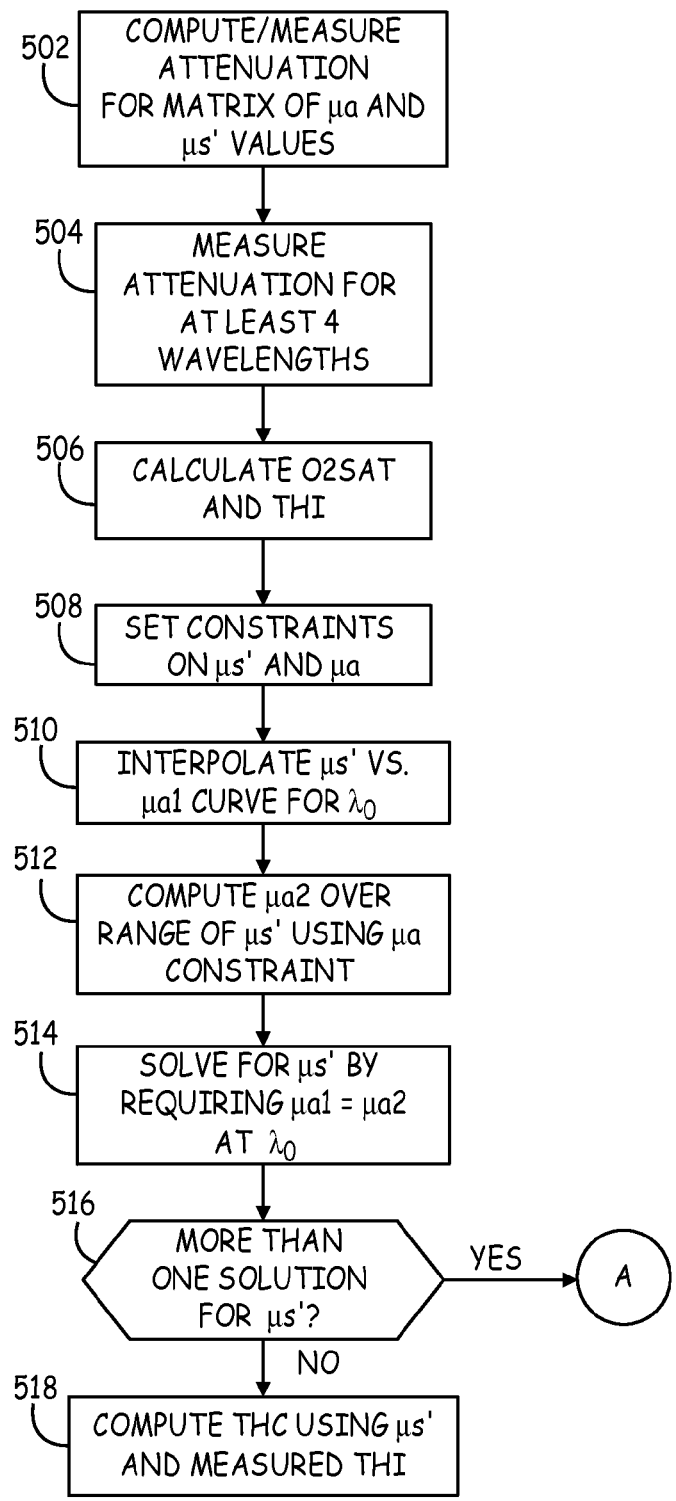
FIG. 9 is a flow chart of an alternative method for measuring THC using attenuation measurements obtained at a single separation distance.

FIG. 9 is a flow chart 500 of an alternative method for measuring THC using attenuation measurements obtained at a single separation distance. In the methods described above involving attenuation measurements at two separation distances, the attenuation measurement at the second separation distance provides additional data needed to solve for four unknowns. Alternatively, constraints may be applied to µs' and µa to limit the solution. At block 502, the attenuation A is computed using a Monte Carlo solution (or measured using tissue phantoms) for a predefined matrix of µa and µs' values. A look up table of µa and µs' values for the computed attenuation A values or a best fit equation is determined. Block 502 is therefore performed a priori and the data is stored in the IMD or other device being used to monitor THC.

At block 504, attenuation is measured for at least four spaced-apart wavelengths for a single emitter-to-detector separation distance. Using the four wavelength measurements, a scaled second derivative measurement of $O_2Sat$ is computed at block 506 as described in the above-incorporated '322 application. A tissue hemoglobin index (THI) is also computed at block 506. THI is computed using the second derivative of attenuation at a wavelength of 760 nm according to the following equation:

$$THI=(M(S2D) \times D760)/SF \quad \{4\}$$

wherein M(S2D), or alternatively M($O_2Sat$), is stored in a look-up table or as an equation during calibration of the sensor. SF is a spacing factor that is not needed when the separation distance used during measurements is the same as the separation distance used during calibration.

THI is considered an index of the hemoglobin present in the tissue in that hemoglobin will cause attenuation of light at 760 nm. THI can be used to verify that the sensor is well positioned against a tissue of interest for monitoring $O_2Sat$ but THI has not been found to correlate well with tissue hemoglobin concentration in vivo and is a unitless measurement that has limited clinical meaning. As such, computation of a calibrated THC in units of mass per unit volume that is correlated to tissue hemoglobin is desirable as it will provide greater clinical meaning relating to the perfusion of the tissue. THC may not correlate well to the concentration of hemoglobin in blood because of vasocontrol, but does yield a definitive measure of concentration of hemoglobin in tissue which is more clinically useful than THI.

THC provides a clinician with more meaningful and useful data, particularly in a chronically implantable device used to monitor the patient or control therapies. Computation of THI, while having limited clinical utility itself in part because it includes tissue scattering artifact, can provide an additional constraint applied in solving a set of equations for µs'.

At block 508, constraints are applied to µs' and µa to limit the solution for µs' using attenuation measured at a single separation distance. Without constraining the solution for µs' and µa, µs' may still be solved for using a multi-variable optimization, however, this optimization takes substantial computation time. The computation time can be dramatically reduced to a more direct solution for µs' by applying constraints. This reduced computation time and power is desirable in chronic implant applications because of the power and time it takes for a multi-variable optimization algorithm. The reduced computational time may also be desirable for acute and external patient monitoring applications because the multi-variable optimization takes up to several seconds and some applications may require faster sampling.

In one embodiment, the constraints on µs' and µa are applied using the following:

$$\mu s'(\lambda)=\mu s'(\lambda_0)*(\lambda/\lambda_0)^{-B} \quad \{5\}$$

$$\mu a(\lambda)=THC*(O_2Sat\, \sigma_{HbO2}+(1-O_2Sat)\sigma_{Hb} \quad \{6\}$$

$$THC=(C1*\mu s'(\lambda_0)+C2) \times THI+w \quad \{7\}$$

In Eqn. 5, $\lambda_0$ is any one of the selected four (or more) wavelengths at which attenuation is being measured. In Eqn. 6, $\sigma_{HbO2}$ and $\sigma_{Hb}$ are the known absorption cross-sections of oxygenated and deoxygenated hemoglobin. These values can be obtained from a table of values given a measured $O_2Sat$. In Eqn. 6, $O_2Sat$ is expressed as a fraction. If measured expressed as a percentage, the percentage should be divided by 100 to obtain the fractional measure of $O_2Sat$. Note that the term $(C1*\mu s'(\lambda_0)+C2)$ in Eqn. 7 is equivalent to M(µs') in Eqn. 2 above. Eqn. 4 defining THI may be substituted for THI in Eqn. 7. The values of calibration constants C1 and C2 in Eqn. 7 will be different for different values of $\lambda_0$ so the selection of $\lambda_0$ is somewhat arbitrary, although a particular wavelength may be preferred in some applications. For example, µs'(760 nm) may be preferred because it may have the best representative indication of the influence of scattering on D760, which is used to compute THC.

At block 510, an interpolated curve (or equation) for µs' and µa is found for the attenuation measured at $\lambda_0$ using data generated a priori at block 502. Plot 350 or plot 352 shown in FIG. 7 are each examples of a three dimensional plot of attenuation A obtained a priori for known ranges of µa and µs'. Only one set of data 350 or 352 is required to interpolate the µa1 vs. µs' curve. Using the same separation distance during patient monitoring (or including a separation distance correction factor), a measured A during patient monitoring is used to isolate a curve defining µa vs. µs' from the three-dimensional surface, e.g. as shown in plot 350 or plot 352 of FIG. 7. The values for µa across the range of µs' values for the measured A is denoted as µa1.

At block 512, µa2 is computed over the same range of µs' values as µa1 for the selected $\lambda_0$ using Eqns. 6 and 7 above. After substituting Eqn. 7 for the THC term in Eqn. 6 the following equation is used to compute µa2:

$$\mu a2 = \{(C1 \cdot \mu s'(\lambda_0) + C2) \times THI + w\} \times (O_2 Sat \, \sigma_{HbO2} + (1 - O_2 Sat) \sigma_{Hb}) \quad \{8\}$$

A solution for µa is constrained to the values of µa1 interpolated from the a priori acquired data (e.g. plot 350) for the selected wavelength and to the values of µa2 computed using Eqn. 8. At this point, µa can be solved for by requiring that µa1 equals µa2 for at the selected wavelength $\lambda_0$. An iterative (or other numerical) solution can be performed at block 514 to determine a solutions for µa and µs' that meet these requirements.

Once µs' is found for the selected wavelength $\lambda_0$, THC is computed at block 518 using Eqn. 7. In Eqn. 7, C1 and C2 are calibration coefficients that are known from a previously-performed calibration procedure using curve fitting methods applied to actual attenuation measurements, as described above.

In some cases, the computation at block 514 may yield more than one solution for µs'($\lambda_0$) as determined at decision block 516. To resolve which solution is correct, an additional constraint may be defined to choose a solution. Additional computations may be needed at wavelengths other than $\lambda_0$ to select a solution for µs'. If the solution for µs' yields more than one solution, the process may advance to the flow chart 600 in FIG. 10, as indicated by the reference A.

Figure 11:
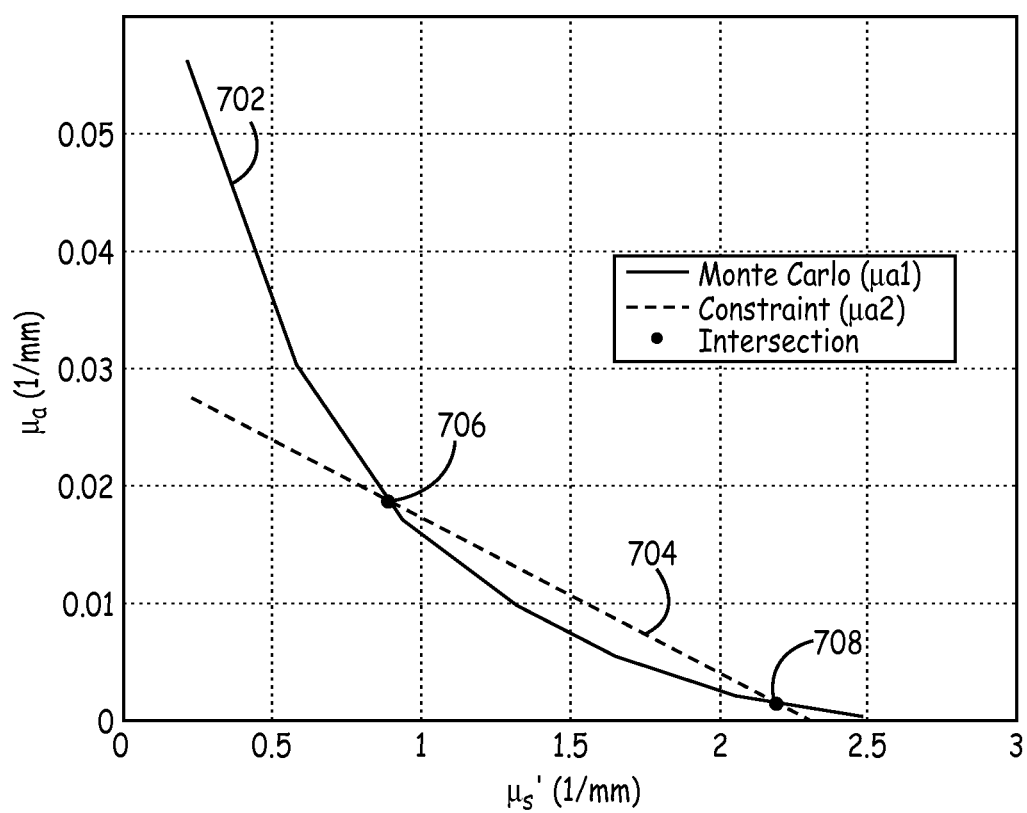
FIG. 11 is a graph $\mu s'$ plotted vs. $\mu a$ as determined for attenuation at a selected wavelength $\lambda_0$.

FIG. 11 is a graph µs' plotted vs. µa as determined for attenuation at a selected wavelength $\lambda_0$. The curve 702 is a plot of µa1 over the range of µs' values for a given attenuation measurement at $\lambda_0$. For a known attenuation measurement, the curve 702 is interpolated from the empirically-derived, three-dimensional plot generated using the Monte Carlo solution or measurements in tissue phantoms, such as plot 350 or 352 in FIG. 7. Curve 702 can be thought of as the intersection of the three-dimensional surface with a plane equal to the measured attenuation. Curve 702 is the curve that is interpolated at block 510 in FIG. 9.

The line 704 represents µa2 computed using Eqn. 8 as described above, at block 512 of FIG. 9. In this example, the curve 702 and the line 704 intersect at two points 706 and 708, yielding two possible solutions for µs'. An added constraint narrowing the possible range of µs' may be applied depending on the monitoring application. Generally, µs' is greater than 0.2 for light scattering tissues at the wavelengths of interest. Some bodily fluids such as cerebral fluids, or some solids such as tooth enamel may have µs' less than 0.2. So in some cases, narrowing the possible range of µs' may reduce the number of solutions to one.

In the example shown in FIG. 11, µs' is constrained to be greater than 0.2, but two possible solutions at points 706 and 708 remain. In this case, additional steps are taken to select the correct solution. If only one intersection occurs between µa1 (curve 702) and µa2 (line 704) within a constrained range of possible µs' values, the solution for µs' is known and THC may be computed directly at block 518 of FIG. 9.

Figure 10:
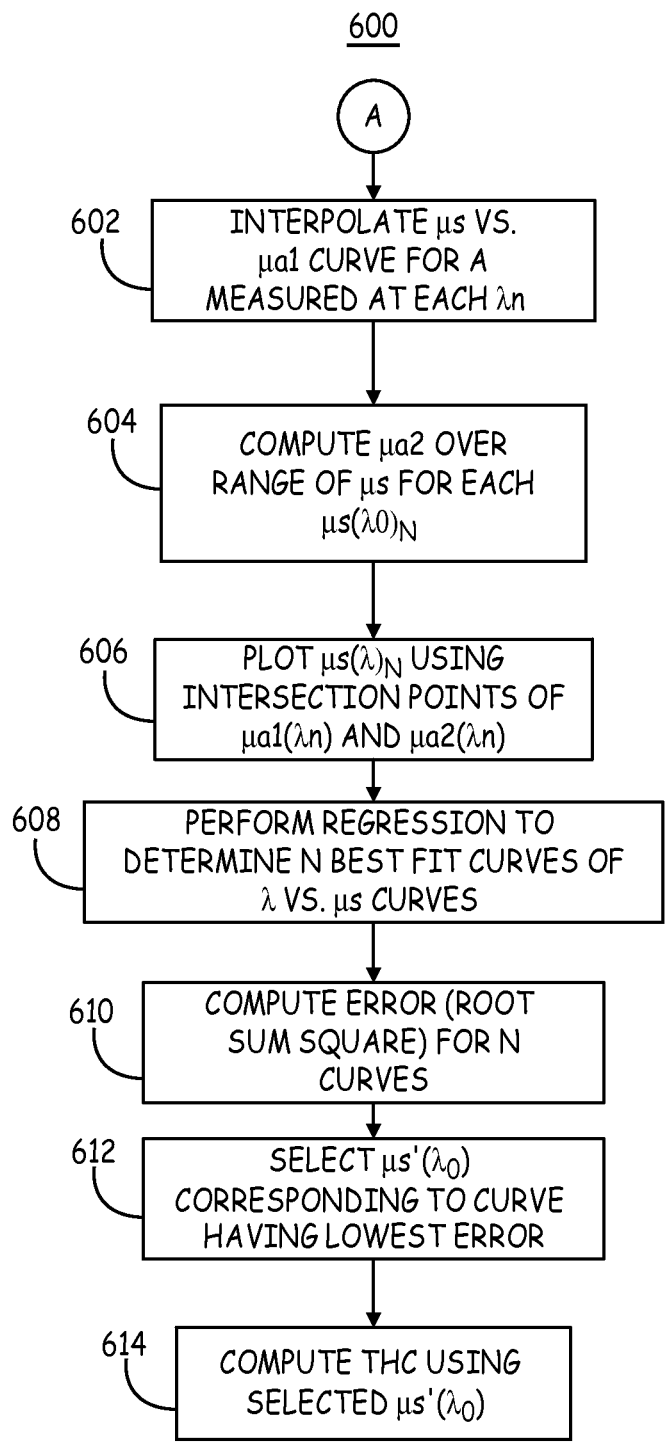
FIG. 10 is a flow chart for selecting a solution for $\mu s'$.

FIG. 10 is a flow chart 600 for resolving a solution for µs' when more than one solution satisfies the above-described equations and constraints. In one embodiment, if two or more solutions remain after limiting the possible range of µs', determinations of µa1 and µa2 are repeated for other wavelengths to provide additional data points for defining µs'($\lambda$) and enable a correct solution of µs'($\lambda_0$) to be identified. For example, if attenuation measurements have been performed for the wavelengths 680 nm, 720 nm, 760 nm, and 800 nm, and 800 nm is selected as $\lambda_0$, a curve defining µs' versus µa1 is interpolated at block 602 using the attenuation measured at each of the other wavelengths and the a priori data acquired and stored in the form of a look-up table or best fit equations, such as the data shown in the plots 350 or 352 of FIG. 7.

At block 604, µa2 is computed as a constant using Eqn. 8 above for each of the N solutions for µs' (two solutions given by points 706 and 708 in the example shown in FIG. 11). In Eqn. 8, THI and O₂Sat are known measurements computed from the second derivative at 760 nm and the scaled second derivative at 720 nm, respectively. The values for C1, C2, $\sigma_{HbO2}$ and $\sigma_{Hb}$ are stored values. Only µs' is unknown. The intersection points 706 and 708 of µa1($\lambda_0$) and µa2($\lambda_0$) as shown in FIG. 11 are used to determine two µs' values that can be substituted into Eqn. 8 to obtain two values for µa2 at each of the other wavelengths, 680 nm, 720 nm, and 760 nm, in the illustrative example.

Figure 12A:
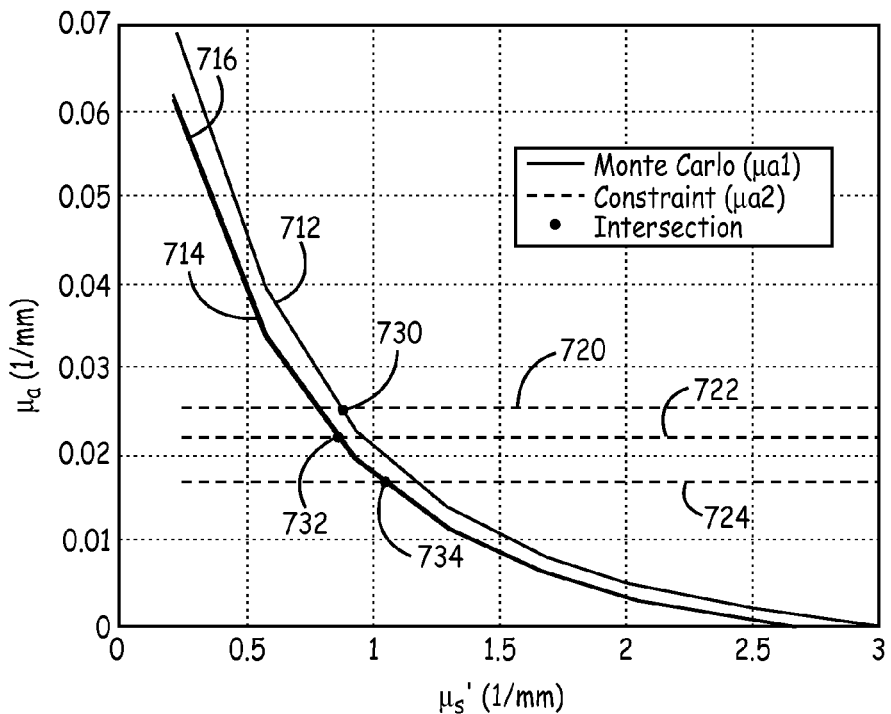
FIGS. 12A and 12B are plots of $\mu s'$ versus $\mu a1(\lambda_n)$ and $\mu a2(\lambda_n)$, respectively, as determined in the method shown in FIG. 10.
Figure 12B:
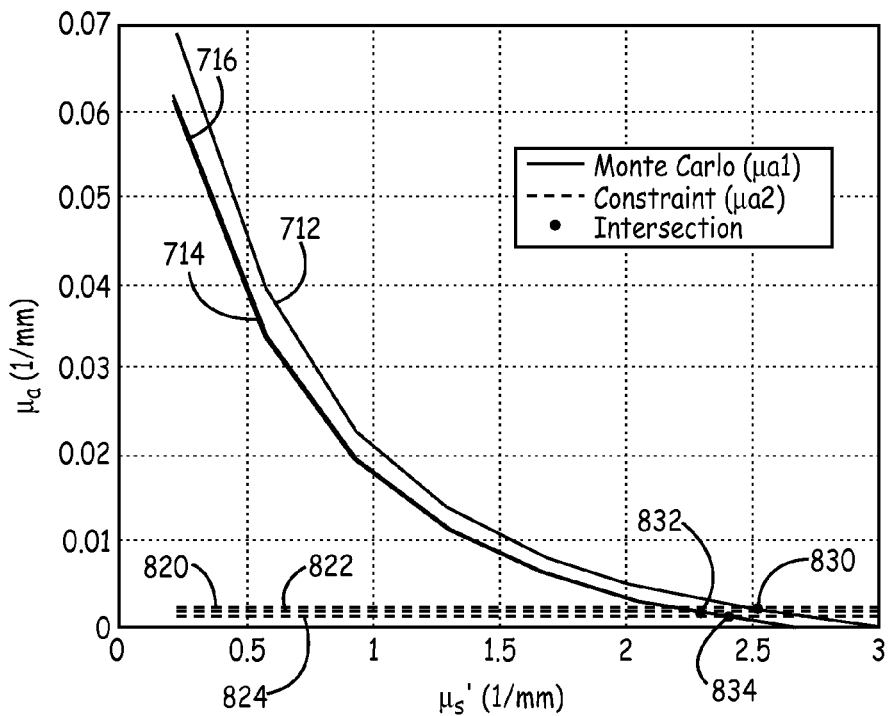

FIGS. 12A and 12B are plots of µs' versus µa1 ($\lambda_n$) and µa2($\lambda_n$), respectively, as determined in blocks 602 and 604 of flow chart 600. In FIGS. 12A and 12B, curve 712 represents µa1 (680 nm) as a function of µs'. Curve 712 is extracted from the intersection of the attenuation measurement at 680 nm and the three-dimensional plot data of A, µa, and µs', e.g. as shown in plot 350 of FIG. 7. Curves 714 and 716 (which are substantially overlapping in this example) represent µa1(720) and µa1(760) over the range of µs' values. These curves 714 and 716 are also extracted from the a priori data obtained from the Monte Carlo solution or from tissue phantom measurements that are stored in the monitoring device in the form of a best fit equation or look-up table of values.

In FIG. 12A, µa2(680 nm), µa2(720 nm) and µa2(760 nm) are each computed using Eqn. 8 above using the first solution of µs', e.g. µs'($\lambda_0$) at intersection point 706 in FIG. 11. In Eqn. 8, the values for $\sigma_{HbO2}$ and $\sigma_{Hb}$ will be different for the different wavelengths. As such, each µa2($\lambda_n$) will have a different value for the same solution of µs'($\lambda_0$). Each of µa2 (680 nm), µa2(720 nm) and µa2(760 nm) are computed as constants and plotted as lines 720, 722 and 724, respectively, resulting in a single intersection with the corresponding curves 712, 714, and 716 of µa1(680 nm), µa1(720), and µa1(760), respectively. These three intersection points 730, 732, and 734 between µa1 and µa2 for a given wavelength yield three possible solutions for µs' at the respective wavelengths of 680 nm, 720 nm, and 760 nm.

Similarly, in FIG. 12B, lines 820, 822, and 824 are the values computed for µa2(680 nm), µa2(720), and µa2(760) using the second solution of µs'($\lambda_0$), e.g. intersection point 708 of FIG. 11, and respective values for $\sigma_{HbO2}$ and $\sigma_{Hb}$ at each wavelength. The resulting three intersection points of $\mu a1(\lambda_n)$ and $\mu a2(\lambda_n)$ in FIG. 12B for each of the three wavelengths yields three additional values for $\mu s'(\lambda_n)$. As such, for each solution of $\mu s'(\lambda_o)$, there are three additional points defined by the intersections shown in FIG. 12A and in FIG. 12B which yields a total of 4 points for defining a curve of $\mu s'$ as a function of wavelength.

Figure 13:
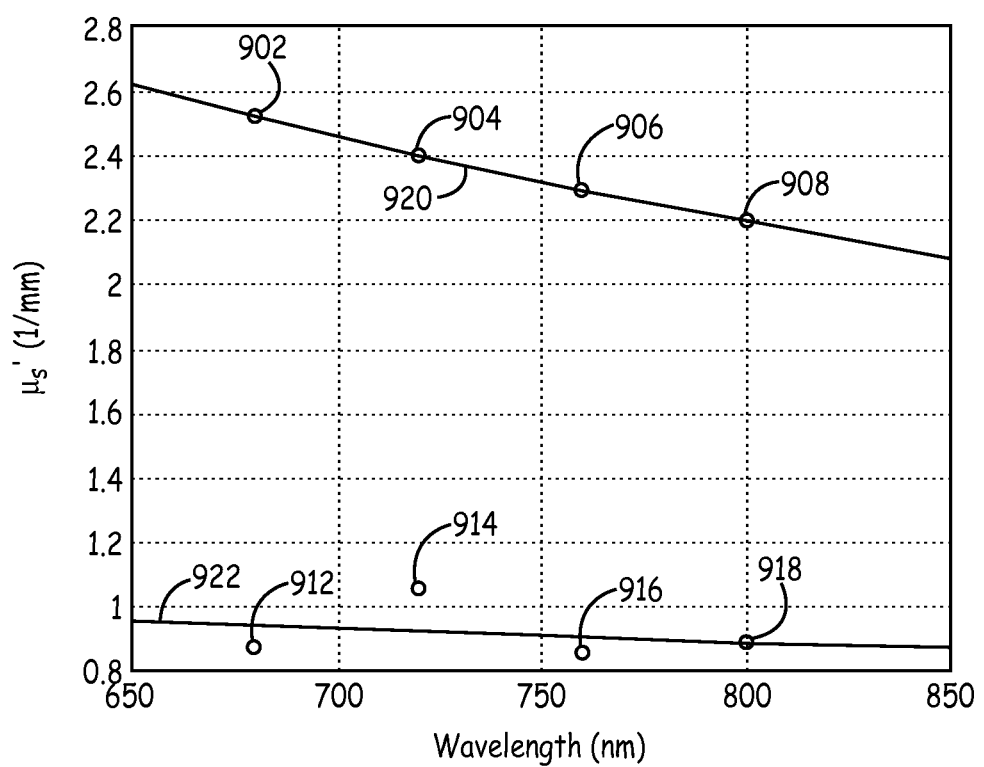
FIG. 13 is a plot of $\mu s'(\lambda)$.

Referring again to FIG. 10, the three additional values of $\mu s'(\lambda_n)$ and the associated solution for $\mu s'(\lambda_O)$ are plotted as a function of wavelength at block 606. FIG. 13 is a plot of $\mu s'$ as a function of wavelength. The N possible solutions for $\mu s'(\lambda_0)$ (e.g., as shown in FIG. 11) and the associated solutions for $\mu s'(\lambda n)$ at other wavelengths (e.g. as shown in FIGS. 12A and 12B) are plotted over wavelength.

The first solution for $\mu s'(\lambda_o)$ (from point 706 in FIG. 11) and corresponding values for $\mu s'(680\ nm)$, $\mu s'(720\ nm)$ and $\mu s'(760\ nm)$ calculated using this first solution, shown as intersection points 730, 732 and 734 in FIG. 12A, respectively, are plotted as points 912, 914, 916, and 918 in FIG. 13.

Similarly, the second solution for $\mu s'(\lambda_o)$ (from point 708 in FIG. 11) and associated values for $\mu s'(680\ nm)$, $\mu s'(720\ nm)$ and $\mu s'(760\ nm)$ shown as intersection points 830, 832 and 834 in FIG. 12B, respectively, are plotted as points 902, 904, 906, and 908 in FIG. 13.

At block 608 of flow chart 600, a least squares regression is performed on each of these sets of points 902 through 908 and 912 through 918 to determine the best fit curves 920 and 922, which may be defined by Eqn. 5 above. The root sum square of the difference between the curve and discrete points is computed at block 610 for the N curves defining $\mu s'(\lambda)$, e.g. curves 920 and 922 in FIG. 13, to determine which best fit curve has the minimum error. In this example, curve 920 has the smallest error based on the root sum square (and as can be seen visually when compared to curve 922 since all points 902 through 908 appear to fall substantially on curve 920).

At block 612, the solution for $\mu s'(\lambda_o)$ yielding the $\mu s'(\lambda)$ best fit curve having minimum error (e.g. curve 902 in FIG. 13) is selected as the solution for $\mu s'(\lambda_o)$. This solution for $\mu s'(\lambda_o)$ is used to compute THC at block 614 according to Eqn. 7. In this way, a solution for $\mu s'$ can be computed in a computationally efficient manner using attenuation measured at a single separation distance to enable a calibrated measure of THC to be performed in a practical manner in an implantable or external device for monitoring a patient in either chronic or acute applications.

Thus, a medical device system and associated method for monitoring THC have been presented in the foregoing description with reference to specific embodiments. It is appreciated that various modifications to the referenced embodiments may be made without departing from the scope of the present disclosure as set forth in the following claims.

The invention claimed is:

1. A method for monitoring tissue hemoglobin concentration using a medical device having an optical sensor, the method comprising:
   measuring light attenuation using the optical sensor positioned adjacent to a volume of tissue;
   determining a value of a tissue scattering coefficient corresponding to the tissue volume in response to the attenuation measurement;
   determining a second derivative of the light attenuation measurement;
   computing an artifact correction term in response to the determined tissue scattering coefficient; and
   computing a tissue hemoglobin concentration in response to the artifact correction term and the second derivative.

2. The method of claim 1 wherein determining a value of a tissue scattering coefficient comprises:
   setting ranges of values for coefficients comprising a range of values for the tissue scattering coefficient and a range of values for a tissue absorption coefficient;
   obtaining light attenuation data corresponding to the ranges of values for coefficients;
   determining a mathematical model of the light attenuation data and the ranges of values for coefficients;
   storing the mathematical model in the medical device; and
   interpolating a solution of the tissue scattering coefficient for the volume of tissue from the mathematical model in response to light attenuation measured at a selected wavelength.

3. The method of claim 2, wherein determining a value of a tissue scattering coefficient further comprises:
   determining a first range of a tissue absorption coefficient from the mathematical model for light attenuation measured at the selected wavelength over the range of values for the tissue scattering coefficient;
   determining a scaled second derivative of the light attenuation;
   determining a second range of the tissue absorption coefficient over the range of values for the tissue scattering coefficient in response to the second derivative and the scaled second derivative;
   determining a constraint of the first range and the second range of the tissue absorption coefficient; and
   determining the tissue scattering coefficient at the selected wavelength to satisfy the constraint applied to the first range and the second range of the tissue absorption coefficient.

4. The method of claim 3, wherein determining a constraint comprises requiring the first range and the second range to yield equal values of the tissue absorption coefficient at the selected wavelength.

5. The method of claim 3, wherein determining the tissue scattering coefficient results in more than one solution, the method further comprising:
   determining a third range of a tissue absorption coefficient from the mathematical model over the range of values for the tissue scattering coefficients and corresponding to attenuation measured at a second wavelength;
   computing a first constant value for the tissue absorption coefficient corresponding to the second wavelength in response to a first solution for the tissue scattering coefficient at the selected wavelength;
   computing a second constant for the tissue absorption coefficient corresponding to the second wavelength in response to a second solution for the tissue scattering coefficient at the selected wavelength;
   determining a first solution for the tissue scattering coefficient at the second wavelength in response to the first constant and the third range of the tissue absorption coefficient;
   determining a second solution for the tissue scattering coefficient at the second wavelength in response to the second constant and the third range of the tissue absorption coefficient;
   performing a first regression using the first solution for the tissue scattering coefficient at the selected wavelength and the first solution for the tissue scattering coefficient at the second wavelength;
   performing a second regression using the second solution for the tissue scattering coefficient at the selected wavelength and the second solution for the tissue scattering coefficient at the second wavelength;

determining the value of the tissue scattering coefficient in response to the first regression and the second regression.

6. The method of claim 2, wherein determining a mathematical model comprises determining a best fit equation relating the tissue scattering coefficient, the tissue absorption coefficient and the light attenuation data.

7. The method of claim 2, wherein determining a mathematical model comprises tabulating a look up table of values relating the tissue scattering coefficient, the tissue absorption coefficient, and the light attenuation data.

8. The method of claim 2, wherein the optical sensor comprises a light emitting portion and a light detecting portion configured to comprise a first emitting-to-detecting separation distance and a second emitting-to-detecting separation distance, and wherein determining a mathematical model comprises obtaining first light attenuation data using the first separation distance and obtaining second light attenuation data using the second separation distance.

9. The method of claim 8, wherein determining a mathematical model further comprises performing a regression and coordinate transformation of the first and second light attenuation data to determine a model of the tissue scattering coefficient as a function the first light attenuation data and the second light attenuation data.

10. The method of claim 1 further comprising:
determining a first scaled second derivative of light attenuation using a first separation distance between a light emitting portion and a light detecting portion of the optical sensor;
determining a second scaled second derivative of light attenuation using a second separation distance between a light emitting portion and a light detecting portion of the optical sensor;
comparing the first and second scaled second derivatives; and
determining the tissue hemoglobin concentration as a valid measurement in response to the first and second scaled second derivatives being approximately equal.

11. A medical device system for monitoring tissue hemoglobin concentration, comprising:
an optical sensor to sense light attenuation in a volume of tissue; and
a processor coupled to the optical sensor configured to measure light attenuation for at least four wavelengths, determine a value of a tissue scattering coefficient corresponding to the tissue volume in response to the measured light attenuation, determine a second derivative of the measured light attenuation, compute an artifact correction term in response to the determined tissue scattering coefficient, and compute a tissue hemoglobin concentration in response to the artifact correction term and the second derivative.

12. The system of claim 11, further comprising a memory, wherein the processor is configured to determine a range of values for the tissue scattering coefficient and a range of values for a tissue absorption coefficient, obtain light attenuation data corresponding to the ranges of values for the coefficients, and determine a mathematical model of the light attenuation data and the ranges of values for the coefficients, the memory storing the mathematical model, and wherein the processor is further configured to interpolate a solution of the tissue scattering coefficient for the volume of tissue from the mathematical model stored in the memory in response to light attenuation measured at a selected wavelength.

13. The system of claim 12, wherein the processor is configured to determine the value of the tissue scattering coefficient by determining a first range of a tissue absorption coefficient from the mathematical model for light attenuation measured at the selected wavelength over the range of values for the tissue scattering coefficient, determine a scaled second derivative of the light attenuation, determine a second range of the tissue absorption coefficient over the range of values for the tissue scattering coefficient in response to the second derivative and the scaled second derivative, determine a constraint of the first range and the second range of the tissue absorption coefficient, and determine the tissue scattering coefficient at the selected wavelength to satisfy the constraint applied to the first range and the second range of the tissue absorption coefficient.

14. The system of claim 13, wherein the processor is further configured to require the first range and the second range to yield equal values of the tissue absorption coefficient at the selected wavelength.

15. The system of claim 13, wherein determining the tissue scattering coefficient yields more than one possible solution, the processor further configured to:
determine a third range of a tissue absorption coefficient from the mathematical model over the range of values for the tissue scattering coefficients and corresponding to attenuation measured at a second wavelength,
determine a first constant value for the tissue absorption coefficient corresponding to the second wavelength in response to a first solution for the tissue scattering coefficient at the selected wavelength,
determine a second constant for the tissue absorption coefficient corresponding to the second wavelength in response to a second solution for the tissue scattering coefficient at the selected wavelength,
determine a first solution for the tissue scattering coefficient at the second wavelength in response to the first constant and the third range of the tissue absorption coefficient,
determine a second solution for the tissue scattering coefficient at the second wavelength in response to the second constant and the third range of the tissue absorption coefficient,
perform a first regression using the first solution for the tissue scattering coefficient at the selected wavelength and the first solution for the tissue scattering coefficient at the second wavelength,
perform a second regression using the second solution for the tissue scattering coefficient at the selected wavelength and the second solution for the tissue scattering coefficient at the second wavelength, and
determine the value of the tissue scattering coefficient in response to the first regression and the second regression.

16. The system of claim 12, wherein the processor is further configured to determine the mathematical model by determining a best fit equation relating the tissue scattering coefficient, the tissue absorption coefficient and the light attenuation data.

17. The system of claim 12, wherein the processor is further configured to determine the mathematical model by tabulating a look up table of values relating the tissue scattering coefficient, the tissue absorption coefficient, and the light attenuation data.

18. The system of claim 12, wherein the optical sensor comprises a light emitting portion and a light detecting portion configured to comprise a first emitting-to-detecting separation distance and a second emitting-to-detecting separation distance, and wherein the processor is configured to determine the mathematical model by obtaining first light attenuation data using the first separation distance and obtaining second light attenuation data using the second separation distance.

19. The system of claim 18, wherein the processor is further configured to determine the mathematical model by performing a regression and coordinate transformation of the first and second light attenuation data to establish a model of the tissue scattering coefficient as a function the first light attenuation data and the second light attenuation data.

20. The system of claim 11, wherein the processor is further configured to determine a first scaled second derivative of light attenuation using a first separation distance between a light emitting portion and a light detecting portion of the optical sensor;
   determine a second scaled second derivative of light attenuation using a second separation distance between a light emitting portion and a light detecting portion of the optical sensor;
   compare the first and second scaled second derivatives; and
   determine the tissue hemoglobin concentration as a valid measurement in response to the first and second scaled second derivatives being approximately equal.

21. A computer-readable medium storing a set of instructions which cause a processor of an implantable medical device system including an optical sensor to:
   measure light attenuation in a volume of tissue, the light attenuation measurement comprising light attenuation measured for at least four wavelengths;
   determine a value of a tissue scattering coefficient corresponding to the tissue volume in response to the attenuation measurement;
   determine a second derivative of the light attenuation measurement;
   determine an artifact correction term in response to the established tissue scattering coefficient; and
   determine a tissue hemoglobin concentration using the artifact correction term and the second derivative.

\* \* \* \* \*